US008648176B2

(12) United States Patent
Davis Orcutt et al.

(10) Patent No.: US 8,648,176 B2
(45) Date of Patent: Feb. 11, 2014

(54) ENGINEERED PROTEINS WITH HIGH AFFINITY FOR DOTA CHELATES

(75) Inventors: Kelly Davis Orcutt, Somerville, MA (US); Karl Dane Wittrup, Chestnut Hill, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 127 days.

(21) Appl. No.: 12/715,162

(22) Filed: Mar. 1, 2010

(65) Prior Publication Data

US 2010/0254987 A1 Oct. 7, 2010

Related U.S. Application Data

(60) Provisional application No. 61/156,467, filed on Feb. 27, 2009.

(51) Int. Cl.
*C07K 16/00* (2006.01)

(52) U.S. Cl.
USPC .................. 530/388.9; 530/388.3; 530/388.6; 530/388.4; 530/387.1; 530/387.3

(58) Field of Classification Search
USPC .......... 530/387.1, 387.3, 387.7, 388.4, 388.6, 530/388.8, 388.9, 388.3
See application file for complete search history.

(56) References Cited

U.S. PATENT DOCUMENTS

| | | | |
|---|---|---|---|
| 2005/0026263 A1 | 2/2005 | Meares et al. |
| 2005/0100543 A1 | 5/2005 | Hansen et al. |
| 2006/0063209 A1 | 3/2006 | Meares et al. |
| 2008/0253964 A1 | 10/2008 | McBride et al. |

FOREIGN PATENT DOCUMENTS

WO 2007/131242 A2 11/2007

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
DeNardo et al. (Cancer Biother. Radiopharm. Dec. 2001; 16 (6): 525-35).*
Axworthy, D.B. et al., "Cure of human carcinoma xenografts by a single dose of pretargeted yttrium-90 with negligible toxicity," PNAS, vol. 97(4):1802-1807 (2000).
Chang, Chien-Hsing et al., "Molecular Advances in Pretargeting Radioimmunotherapy with Bispecific Antibodies," Molecular Cancer Therapeutics, vol. 1:553-563 (2002).
Chao, Ginger et al., "Isolating and engineering human antibodies using yeast surface display," Nature Protocols, vol. 3(2):755-768 (2006).
Corneillie, Todd M. et al., "Crystal Structures of Two Complexes of the Rare-Earth-DOTA-Binding Antibody 2D12.5: Ligand Generality from a Chiral System," J. Am. Chem. Soc., vol. 125:15039-15048 (2003).
Corneillie, Todd M. et al., "Irreversible Engineering of the Multielement-Binding Antibody 2D12.5 and Its Complementary Ligands," Bioconjugate, vol. 15:1392-1402 (2004).
Gai, S. Annie et al., "Yeast surface display for protein engineering and characterization," Current Opinion in Structural Biology, vol. 17:467-473 (2007).
Gautherot, Emmanuel et al., "Pretargeted Radioimmunotherapy of Human Colorectal Xenografts with Bispecific Antibody and 131I-Labeled Bivalent Hapten," The Journal of Nuclear Medicine, vol. 41(3):480-487 (2000).
Graff, Christilyn P. et al., "Directed evolution of an anti-carcinoembryonic antigen scFv with a 4-day monovalent dissociation half-time at 37 deg. C," Protein Engineering, Design & Selection, vol. 17(4):293-304 (2004).
Karacay, Habibe et al., "Therapeutic Advantage of Pretargeted Radioimmunotherapy Using a Recombinant Bispecific Antibody in a Human Colon Cancer Xenograft," Clinical Cancer Research, vol. 11(21):7879-7885 (2005).
Knox, Susan J. et al., "Phase II Trial of Yttrium-90-DOTA-Biotin Pretargeted by NR-LU-10 Antibody/Streptavidin in Patients with Metastatic Colon Cancer," Clinical Cancer Research, vol. 6:406-414 (2000).
Kraeber-Bodere, Francoise et al., "Targeting, Toxicity, and Efficacy of 2-Step, Pretargeted Radioimmunotherapy Using a Chimeric Bispecific Antibody and 131I-Labeled Bivalent Hapten in a Phase I Optimization Clinical Trial," J. Nucl. Med., vol. 47:247-255 (2006).
Kraeber-Bodere, Francoise et al., "Toxicity and Efficacy of Radioimmunotherapy in Carcinoembryonic Antigen-producing Medullary Thyroid Cancer Xenograft: Comparison of Iodine 131-labeled F(ab')2 and Pretargeted Bivalent Hapten and Evaluation of Repeated Injections," Clinical Cancer Research, vol. 5:3183s-3189s (1999).
Le Mignon, Marie-Madeleine et al., "Pharmacokinetics and Tolerability After Intravenous Injection into Healthy Volunteers," Investigative Radiology, vol. 25(8):933-937 (1990).

(Continued)

*Primary Examiner* — Stephen Rawlings
(74) *Attorney, Agent, or Firm* — Nelson Mullins Riley & Scarborough LLP; Amy E. Mandragouras, Esq.; Christopher L. Frank

(57) ABSTRACT

The present invention features, inter alia, compositions and methods for the treatment of cancer and infectious disease. The compositions include engineered proteins that specifically bind a metal chelate and may be bispecific. For example, the engineered proteins may bind (a) a target (e.g., a cellular protein) on a cancerous cell or a pathogen and (b) a metal chelate comprising DOTA, or an active variant thereof, and a metal ion such as a radionuclide. By virtue of the multiple binding sites, the engineered protein effectively delivers a metal chelate to a cell one wishes to destroy.

40 Claims, 10 Drawing Sheets

(56) References Cited

OTHER PUBLICATIONS

Orcutt, Kelly Davis et al., "A modular IgG-scFv bispecific antibody topology," Protein Engineering, Design & Selection, vol. 23(4):221-228 (2010).
Pagel, John M. et al., "Comparison of anti-CD20 and anti-CD-45 antibodies for conventional and pretargeted radioimmunotherapy of B-cell lymphomas," Blood, vol. 101(6):2340-2348 (2003).
Press, Oliver W. et al., "A comparative evaluation of conventional and pretargeted radioimmunotherapy of CD20-expressing lymphoma xenografts," Blood, vol. 98(8):2535-2543 (2001).
Schmidt, Michael M. et al., "A modeling analysis of the effects of molecular size and binding affinity on tumor targeting," Mol. Cancer Ther., vol. 8(10):2861-2871 (2009).
Sharkey, Robert M. et al., "A Universal Pretargeting System for Cancer Detection and Therapy Using Bispecific Antibody," Cancer Research, vol. 63:354-363 (2003).
Sharkey, Robert M. et al., "Metastatic Human Colonic Carcinoma: Molecular Imaging with Pretargeted SPECT and PET in a Mouse Model," Radiology, vol. 246(2):497-507 (2008).
Sharkey, Robert M. et al., "Pretargeted Versus Directly Targeted Radioimmunotherapy Combined with Anti-CD20 Antibody Consolidation Therapy of Non-Hodgkin Lymphoma," The Journal of Nuclear Medicine, vol. 50(3):444-453 (2009).
Sharkey, Robert M. et al., "Signal amplification in molecular imaging by pretargeting a multivalent, bispecific antibody," Nature Medicine, vol. 11(11):1250-1255 (2005).
Van Schaijk, Frank G. et al., "Pretargeting of Carcinoembryonic Antigen—Expressing Tumors with a Biologically Produced Bispecific Anticarcinoembryonic Antigen X Anti-Indium—Labeled Diethylenetriaminepentaacetic Acid Antibody," Clin. Cancer Res., vol. 11(19 Suppl.):7130s-7136s (2005).

* cited by examiner

DOTA-metal

DOTA-Bn-metal

DOTA-Bn-biotin-metal

DOTA-alkyl-biotin-metal

SEQ ID NOs: 2, 4, 6, 8, 10, 12, 14, 16, 18, 20, 22, 24, 26, 28, 30, 32, AND 34 TERMINATE AT RESIDUE 244 OF THE RESPECTIVE CLONES SHOWN HERE.

DATA POINTS REPRESENT AVERAGE +/- STANDARD DEVIATION FOR 3 OR 4 MICE
SOLID LINES REPRESENT A BIEXPONENTIAL FIT TO THE DATA
* FURTHER DOTA TIME POINTS HAD NO MEASUREABLE ACTIVITY

```
                         SEQUENCE LISTING


<160> NUMBER OF SEQ ID NOS: 48

<210> SEQ ID NO 1
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Thr Tyr Ala Ala Phe Ile
    50                  55                  60

Ser Arg Leu Asn Ile Tyr Lys Asp Asn Ser Lys Asn Gln Val Phe Phe
65                  70                  75                  80

Glu Met Asn Ser Leu Gln Ala Asn Asp Thr Ala Met Tyr Tyr Cys Ala
                85                  90                  95

Arg Arg Gly Ser Tyr Pro Tyr Asn Tyr Phe Asp Val Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Gln Ala Val Val Thr Gln Glu Ser Ala Leu
    130                 135                 140

Thr Thr Ser Pro Gly Glu Thr Val Thr Leu Thr Cys Arg Ser Ser Thr
145                 150                 155                 160

Gly Ala Val Thr Thr Ser Asn Tyr Ala Asn Trp Val Gln Glu Lys Pro
                165                 170                 175

Asp His Leu Phe Thr Gly Leu Ile Gly Gly Asn Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Ala Asp Ala Ile Tyr Phe Cys
    210                 215                 220

Ala Leu Trp Tyr Ser Asn His Trp Val Phe Gly Gly Gly Phe Arg Gly
225                 230                 235                 240

Arg Val Leu Gly
```

<210> SEQ ID NO 2
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Thr Ala Ala Phe Ile
    50                  55                  60

Ser Arg Leu Asn Ile Tyr Lys Asp Asn Ser Lys Asn Gln Val Phe Phe
65                  70                  75                  80

Glu Met Asn Ser Leu Gln Ala Glu Asp Thr Ala Met Tyr Tyr Cys Ala
                85                  90                  95

Arg Arg Gly Ser Tyr Pro Tyr Asn Tyr Phe Asp Val Trp Gly Cys Gly
            100                 105                 110

Thr Thr Val Thr Val Ser Ser Gly Gly Gly Gly Ser Gly Gly Gly Gly
        115                 120                 125

Ser Gly Gly Gly Gly Ser Gln Ala Val Val Thr Gln Glu Ser Ala Leu
    130                 135                 140

Thr Thr Ser Pro Gly Glu Thr Val Thr Leu Thr Cys Arg Ser Ser Thr
145                 150                 155                 160

Gly Ala Val Thr Thr Ser Asn Tyr Ala Asn Trp Val Gln Glu Lys Pro
                165                 170                 175

Asp His Cys Phe Thr Gly Leu Ile Gly Gly Asn Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asn His Trp Val Phe Gly Gly Gly Thr Arg Leu
225                 230                 235                 240

Thr Val Leu Gly
```

<210> SEQ ID NO 3
<211> LENGTH: 256
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60
```

```
Ser Arg Leu Asn Ile Tyr Arg Asp Asn Ser Lys Asn Gln Val Phe Leu
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Arg Gly
            100                 105                 110

Thr Thr Val Thr Val Ser Ser Gly Gly Gly Gly Ser Gly Gly Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Gly Gly Thr Arg Leu
225                 230                 235                 240

Thr Val Leu Gly Gly Ser Glu Gln Lys Leu Ile Ser Glu Glu Asp Leu
                245                 250                 255


<210> SEQ ID NO 4
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Arg Gly
            100                 105                 110

Thr Thr Val Thr Val Ser Ser Gly Gly Gly Gly Ser Gly Gly Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175
```

```
Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Gly Gly Thr Arg Leu
225                 230                 235                 240

Thr Val Leu Gly
```

<210> SEQ ID NO 5
<211> LENGTH: 229
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Leu Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Glu Asp Thr Ala Met Tyr Tyr Cys Ala
                85                  90                  95

Arg Arg Gly Ser Tyr Pro Tyr Asn Tyr Phe Asp Ala Trp Gly Arg Gly
            100                 105                 110

Thr Thr Val Thr Val Ser Ser Glu Gly Gly Gly Ser Gly Gly Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Leu
    210                 215                 220

Cys Phe Val Val Phe
225
```

<210> SEQ ID NO 6
<211> LENGTH: 229
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Leu Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Glu Asp Thr Ala Met Tyr Tyr Cys Ala
                85                  90                  95

Arg Arg Gly Ser Tyr Pro Tyr Asn Tyr Phe Asp Ala Trp Gly Arg Gly
            100                 105                 110

Thr Thr Val Thr Val Ser Ser Glu Gly Gly Gly Ser Gly Gly Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Leu
    210                 215                 220

Cys Phe Val Val Phe
225


<210> SEQ ID NO 7
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (247)..(247)
<223> OTHER INFORMATION: Any amino acid

<400> SEQUENCE: 7

Gln Ala Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Cys Gly
```

```
            100                 105                 110

Thr Thr Val Thr Val Ser Ser Gly Gly Gly Gly Ser Gly Gly Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Gly Gly Thr Arg Leu
225                 230                 235                 240

Thr Val Leu Gly Gly Ser Xaa Gln Lys Leu Ile Ser Glu Glu Asp Leu
                245                 250                 255


<210> SEQ ID NO 8
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Ala Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Gly Ser Gly Gly Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
```

```
    210                 215                 220

Ala Leu Trp Tyr Ser Asp His Trp Val Ile Gly Gly Gly Thr Arg Leu
225                 230                 235                 240

Thr Val Leu Gly


<210> SEQ ID NO 9
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (245)..(245)
<223> OTHER INFORMATION: Any amino acid
<220> FEATURE:
<221> NAME/KEY: MOD_RES
<222> LOCATION: (254)..(254)
<223> OTHER INFORMATION: Any amino acid
<220> FEATURE:
<221> NAME/KEY: MOD_RES
<222> LOCATION: (257)..(257)
<223> OTHER INFORMATION: Any amino acid

<400> SEQUENCE: 9

Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Gly Pro Gly Gly Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Gly Gly Thr Arg Leu
225                 230                 235                 240

Thr Val Leu Ser Xaa Ser Glu Gln Lys Leu Ile Ser Glu Xaa Asp Leu
                245                 250                 255

Xaa
```

-continued

<210> SEQ ID NO 10
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Gly Pro Gly Gly Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Gly Gly Thr Arg Leu
225                 230                 235                 240

Thr Val Leu Ser
```

<210> SEQ ID NO 11
<211> LENGTH: 256
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
His Val Lys Leu Gln Glu Ser Gly Pro Gly Leu Val Gln Pro Ser Gln
1               5                   10                  15

Ser Leu Ser Leu Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60
```

Ser Arg Leu Asn Ile Tyr Arg Asp Asn Ser Lys Asn Gln Val Phe Leu
65 70 75 80

Glu Met Asn Ser Leu Gln Ala Glu Asp Thr Ala Met Tyr Tyr Cys Ala
85 90 95

Arg Arg Gly Ser Tyr Pro Tyr Asn Tyr Phe Asp Ala Trp Gly Cys Gly
100 105 110

Thr Thr Val Thr Val Ser Ser Gly Gly Gly Gly Ser Gly Gly Gly Gly
115 120 125

Ser Gly Gly Gly Gly Ser Gln Ala Val Val Ile Gln Glu Ser Ala Leu
130 135 140

Thr Thr Pro Pro Gly Glu Thr Val Thr Leu Thr Cys Gly Ser Ser Thr
145 150 155 160

Gly Ala Val Thr Ala Ser Asn Tyr Ala Asn Trp Val Gln Glu Lys Pro
165 170 175

Asp His Cys Phe Thr Gly Leu Ile Gly Gly His Asn Asn Arg Pro Pro
180 185 190

Gly Val Pro Ala Arg Phe Ser Gly Ser Leu Ile Gly Asp Lys Ala Ala
195 200 205

Leu Thr Ile Ala Gly Thr Gln Thr Glu Asp Glu Ala Ile Tyr Phe Cys
210 215 220

Ala Leu Trp Tyr Ser Asp His Trp Val Ile Gly Gly Gly Thr Arg Leu
225 230 235 240

Thr Val Leu Gly Gly Ser Glu Gln Lys Leu Ile Ser Glu Glu Asp Leu
245 250 255

<210> SEQ ID NO 12
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

His Val Lys Leu Gln Glu Ser Gly Pro Gly Leu Val Gln Pro Ser Gln
1 5 10 15

Ser Leu Ser Leu Thr Cys Thr Val Ser Gly Phe Ser Leu Thr Asp Tyr
20 25 30

Gly Val His Trp Val Arg Gln Ser Pro Gly Lys Gly Leu Glu Trp Leu
35 40 45

Gly Val Ile Trp Ser Gly Gly Gly Thr Ala Tyr Asn Thr Ala Leu Ile
50 55 60

Ser Arg Leu Asn Ile Tyr Arg Asp Asn Ser Lys Asn Gln Val Phe Leu
65 70 75 80

Glu Met Asn Ser Leu Gln Ala Glu Asp Thr Ala Met Tyr Tyr Cys Ala
85 90 95

Arg Arg Gly Ser Tyr Pro Tyr Asn Tyr Phe Asp Ala Trp Gly Cys Gly
100 105 110

Thr Thr Val Thr Val Ser Ser Gly Gly Gly Gly Ser Gly Gly Gly Gly
115 120 125

Ser Gly Gly Gly Gly Ser Gln Ala Val Val Ile Gln Glu Ser Ala Leu
130 135 140

Thr Thr Pro Pro Gly Glu Thr Val Thr Leu Thr Cys Gly Ser Ser Thr
145 150 155 160

Gly Ala Val Thr Ala Ser Asn Tyr Ala Asn Trp Val Gln Glu Lys Pro
165 170 175

```
Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Gly Gly Thr Arg Leu
225                 230                 235                 240

Thr Val Leu Gly


<210> SEQ ID NO 13
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (247)..(247)
<223> OTHER INFORMATION: Any amino acid

<400> SEQUENCE: 13

Gln Val Lys Leu Gln Glu Ser Gly Pro Gly Leu Val Arg Pro Ser Gln
1               5                   10                  15

Pro Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Gly Ser Gly Gly Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Phe Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Gly Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Gly Gly Thr Arg Leu
225                 230                 235                 240

Thr Val Leu Gly Gly Ser Xaa Gln Lys Leu Ile Ser Glu Glu Asp Leu
                245                 250                 255


<210> SEQ ID NO 14
```

<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

```
Gln Val Lys Leu Gln Glu Ser Gly Pro Gly Leu Val Arg Pro Ser Gln
1               5                   10                  15

Pro Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Gly Ser Gly Gly Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Phe Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Gly Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Gly Gly Thr Arg Leu
225                 230                 235                 240

Thr Val Leu Gly
```

<210> SEQ ID NO 15
<211> LENGTH: 256
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Phe
```

```
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Gly Ser Gly Gly Gly Gly
        115                 120                 125

Ser Gly Gly Gly Gly Ser Gln Ala Val Val Ile Gln Glu Ser Ala Leu
    130                 135                 140

Ile Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Gly Asp Glu Ala Ile Tyr Phe Cys
    210                 215                 220

Ala Leu Trp Tyr Ser Asp His Trp Val Ile Gly Gly Gly Thr Arg Leu
225                 230                 235                 240

Thr Val Leu Gly Gly Ser Glu Gln Lys Leu Ile Ser Glu Glu Asp Leu
                245                 250                 255


<210> SEQ ID NO 16
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Phe
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Gly Ser Gly Gly Gly Gly
        115                 120                 125

Ser Gly Gly Gly Gly Ser Gln Ala Val Val Ile Gln Glu Ser Ala Leu
    130                 135                 140

Ile Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
```

```
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Gly Asp Glu Ala Ile Tyr Phe Cys
    210                 215                 220

Ala Leu Trp Tyr Ser Asp His Trp Val Ile Gly Gly Gly Thr Arg Leu
225                 230                 235                 240

Thr Val Leu Gly


<210> SEQ ID NO 17
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Gly Ser Gly Gly Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Gly Gly Thr Arg Leu
225                 230                 235                 240

Thr Val Leu Gly Gly Ser Glu Gln Lys Leu Ile Ser Glu Glu Asp Leu
                245                 250                 255


<210> SEQ ID NO 18
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 18

```
Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Gly Ser Gly Gly Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Gly Gly Thr Arg Leu
225                 230                 235                 240

Thr Val Leu Gly
```

<210> SEQ ID NO 19
<211> LENGTH: 256
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

```
Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Ser Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Lys Asp Asn Ser Lys Asn Gln Val Phe Phe
65                  70                  75                  80

Glu Met Asn Ser Leu Gln Ala Glu Asp Thr Ala Met Tyr Tyr Cys Ala
                85                  90                  95

Arg Arg Gly Arg Tyr Pro Tyr Asn Tyr Phe Asp Ala Trp Gly Cys Gly
```

```
            100                 105                 110

Thr Thr Val Thr Val Ser Ser Gly Gly Gly Gly Ser Gly Gly Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Phe Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Tyr Cys
    210                 215                 220

Ala Leu Trp Tyr Ser Asp His Trp Val Ile Gly Gly Gly Thr Arg Leu
225                 230                 235                 240

Thr Val Leu Gly Gly Ser Glu Gln Lys Leu Ile Ser Glu Glu Asp Leu
                245                 250                 255


<210> SEQ ID NO 20
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Ser Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Lys Asp Asn Ser Lys Asn Gln Val Phe Phe
65                  70                  75                  80

Glu Met Asn Ser Leu Gln Ala Glu Asp Thr Ala Met Tyr Tyr Cys Ala
                85                  90                  95

Arg Arg Gly Arg Tyr Pro Tyr Asn Tyr Phe Asp Ala Trp Gly Cys Gly
            100                 105                 110

Thr Thr Val Thr Val Ser Ser Gly Gly Gly Gly Ser Gly Gly Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Phe Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Tyr Cys
```

```
    210                 215                 220

Ala Leu Trp Tyr Ser Asp His Trp Val Ile Gly Gly Gly Thr Arg Leu
225                 230                 235                 240

Thr Val Leu Gly


<210> SEQ ID NO 21
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (254)..(254)
<223> OTHER INFORMATION: Any amino acid

<400> SEQUENCE: 21

Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Phe
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Gly Ser Gly Ser Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Gly Gly Thr Arg Leu
225                 230                 235                 240

Thr Val Leu Gly Gly Ser Glu Gln Lys Leu Ile Ser Glu Xaa Asp Leu
                245                 250                 255


<210> SEQ ID NO 22
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22
```

-continued

```
Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Phe
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Gly Ser Gly Ser Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Gly Gly Thr Arg Leu
225                 230                 235                 240

Thr Val Leu Gly


<210> SEQ ID NO 23
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Lys Leu Gln Glu Ser Gly Pro Gly Leu Val Gln Pro Pro Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Phe
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110
```

Thr Thr Val Thr Val Ser Ser Gly Gly Gly Gly Ser Gly Gly Gly Gly
115 120 125

Ser Gly Gly Gly Gly Ser Gln Ala Val Val Ile Gln Glu Ser Ala Leu
130 135 140

Thr Thr Ser Pro Gly Glu Thr Val Thr Leu Thr Cys Gly Ser Ser Thr
145 150 155 160

Gly Ala Val Thr Ala Ser Asn Tyr Ala Asn Trp Val Gln Glu Lys Pro
165 170 175

Asp His Cys Phe Thr Gly Leu Ile Gly Gly His Asn Asn Arg Pro Pro
180 185 190

Gly Val Pro Ala Arg Phe Ser Gly Ser Leu Ile Gly Asp Lys Ala Thr
195 200 205

Leu Thr Ile Ala Gly Thr Gln Thr Glu Asp Glu Ala Ile Tyr Phe Cys
210 215 220

Ala Leu Trp Tyr Ser Asp His Trp Val Ile Gly Gly Gly Thr Arg Leu
225 230 235 240

Thr Val Leu Gly Gly Ser Glu Gln Lys Leu Ile Ser Glu Glu Asp Leu
245 250 255

<210> SEQ ID NO 24
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

Gln Val Lys Leu Gln Glu Ser Gly Pro Gly Leu Val Gln Pro Pro Gln
1 5 10 15

Ser Leu Ser Ile Thr Cys Thr Val Ser Gly Phe Ser Leu Thr Asp Tyr
20 25 30

Gly Val His Trp Val Arg Gln Ser Pro Gly Lys Gly Leu Glu Trp Leu
35 40 45

Gly Val Ile Trp Ser Gly Gly Gly Thr Ala Tyr Asn Thr Ala Leu Ile
50 55 60

Ser Arg Leu Asn Ile Tyr Arg Asp Asn Ser Lys Asn Gln Val Phe Phe
65 70 75 80

Glu Met Asn Ser Leu Gln Ala Asp Asp Thr Ala Met Tyr Tyr Cys Ala
85 90 95

Arg Arg Gly Ser Tyr Pro Tyr Asn Tyr Phe Asp Ala Trp Gly Cys Gly
100 105 110

Thr Thr Val Thr Val Ser Ser Gly Gly Gly Gly Ser Gly Gly Gly Gly
115 120 125

Ser Gly Gly Gly Gly Ser Gln Ala Val Val Ile Gln Glu Ser Ala Leu
130 135 140

Thr Thr Ser Pro Gly Glu Thr Val Thr Leu Thr Cys Gly Ser Ser Thr
145 150 155 160

Gly Ala Val Thr Ala Ser Asn Tyr Ala Asn Trp Val Gln Glu Lys Pro
165 170 175

Asp His Cys Phe Thr Gly Leu Ile Gly Gly His Asn Asn Arg Pro Pro
180 185 190

Gly Val Pro Ala Arg Phe Ser Gly Ser Leu Ile Gly Asp Lys Ala Thr
195 200 205

Leu Thr Ile Ala Gly Thr Gln Thr Glu Asp Glu Ala Ile Tyr Phe Cys
210 215 220

Ala Leu Trp Tyr Ser Asp His Trp Val Ile Gly Gly Gly Thr Arg Leu
225 230 235 240

Thr Val Leu Gly

<210> SEQ ID NO 25
<211> LENGTH: 256
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

Gln Val Lys Leu Gln Glu Ser Gly Pro Gly Leu Val Gln Pro Ser Gln
1 5 10 15

Ser Leu Ser Ile Thr Cys Thr Val Ser Gly Phe Ser Leu Thr Asp Tyr
20 25 30

Gly Val His Trp Val Arg Gln Ser Pro Gly Lys Gly Leu Glu Trp Leu
35 40 45

Gly Val Ile Trp Ser Gly Gly Gly Thr Ala Tyr Asn Thr Ala Leu Ile
50 55 60

Ser Arg Leu Asn Ile Tyr Arg Asp Asn Ser Lys Asn Gln Val Phe Phe
65 70 75 80

Glu Met Asn Ser Leu Gln Ala Glu Asp Thr Ala Met Tyr Tyr Cys Ala
85 90 95

Arg Arg Gly Ser Tyr Pro Tyr Asn Tyr Phe Asp Ala Trp Gly Cys Gly
100 105 110

Thr Thr Val Thr Val Ser Ser Gly Gly Gly Gly Pro Gly Gly Gly Gly
115 120 125

Ser Gly Gly Gly Gly Ser Gln Ala Val Val Ile Gln Glu Ser Ala Leu
130 135 140

Thr Thr Ser Pro Gly Glu Thr Val Thr Leu Thr Cys Gly Ser Ser Thr
145 150 155 160

Gly Ala Ile Thr Thr Ser Asn Tyr Ala Asn Trp Val Gln Glu Lys Pro
165 170 175

Asp His Cys Phe Thr Gly Leu Ile Gly Gly His Asn Asn Arg Pro Pro
180 185 190

Gly Val Pro Ala Arg Phe Ser Gly Ser Leu Ile Gly Asp Lys Ala Ala
195 200 205

Leu Thr Ile Ala Gly Thr Gln Thr Glu Asp Glu Ala Ile Tyr Phe Cys
210 215 220

Ala Leu Trp Tyr Ser Asp His Trp Val Ile Gly Gly Gly Thr Arg Leu
225 230 235 240

Thr Val Leu Gly Gly Ser Glu Gln Lys Leu Ile Ser Glu Glu Asp Leu
245 250 255

<210> SEQ ID NO 26
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

Gln Val Lys Leu Gln Glu Ser Gly Pro Gly Leu Val Gln Pro Ser Gln
1 5 10 15

Ser Leu Ser Ile Thr Cys Thr Val Ser Gly Phe Ser Leu Thr Asp Tyr
20 25 30

```
Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Phe
65                  70                  75                  80

Glu Met Asn Ser Leu Gln Ala Glu Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Gly Pro Gly Gly Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Ile Thr Thr Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Gly Gly Thr Arg Leu
225                 230                 235                 240

Thr Val Leu Gly


<210> SEQ ID NO 27
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Glu Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Gly Ser Gly Gly Gly Gly
        115                 120                 125

Ser Gly Gly Gly Gly Ser Gln Ala Val Val Ile Gln Glu Ser Ala Leu
    130                 135                 140
```

Thr Thr Ser Pro Gly Glu Thr Val Thr Leu Thr Cys Gly Ser Ser Thr
145 150 155 160

Gly Ala Val Thr Ala Ser Asn Tyr Ala Asn Trp Val Gln Glu Lys Pro
165 170 175

Asp His Cys Phe Thr Gly Leu Ile Gly Gly His Asn Asn Arg Pro Pro
180 185 190

Gly Val Pro Ala Arg Phe Ser Gly Ser Leu Ile Gly Asp Lys Ala Ala
195 200 205

Leu Thr Ile Val Gly Thr Gln Thr Glu Asp Glu Ala Ile Tyr Phe Cys
210 215 220

Ala Leu Trp Tyr Ser Asp His Trp Val Ile Gly Gly Gly Thr Arg Leu
225 230 235 240

Thr Val Leu Gly Gly Ser Glu Gln Lys Leu Ile Ser Glu Glu Asp Leu
245 250 255

<210> SEQ ID NO 28
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

Gln Val Lys Leu Gln Glu Ser Gly Pro Gly Leu Val Gln Pro Ser Gln
1 5 10 15

Ser Leu Ser Ile Thr Cys Thr Val Ser Gly Phe Ser Leu Thr Asp Tyr
20 25 30

Gly Val His Trp Val Arg Gln Ser Pro Gly Lys Gly Leu Glu Trp Leu
35 40 45

Gly Val Ile Trp Ser Gly Gly Gly Thr Ala Tyr Asn Thr Ala Leu Ile
50 55 60

Ser Arg Leu Asn Ile Tyr Arg Asp Asn Ser Lys Asn Gln Val Phe Leu
65 70 75 80

Glu Met Asn Ser Leu Gln Ala Glu Asp Thr Ala Met Tyr Tyr Cys Ala
85 90 95

Arg Arg Gly Ser Tyr Pro Tyr Asn Tyr Phe Asp Ala Trp Gly Cys Gly
100 105 110

Thr Thr Val Thr Val Ser Ser Gly Gly Gly Gly Ser Gly Gly Gly Gly
115 120 125

Ser Gly Gly Gly Gly Ser Gln Ala Val Val Ile Gln Glu Ser Ala Leu
130 135 140

Thr Thr Ser Pro Gly Glu Thr Val Thr Leu Thr Cys Gly Ser Ser Thr
145 150 155 160

Gly Ala Val Thr Ala Ser Asn Tyr Ala Asn Trp Val Gln Glu Lys Pro
165 170 175

Asp His Cys Phe Thr Gly Leu Ile Gly Gly His Asn Asn Arg Pro Pro
180 185 190

Gly Val Pro Ala Arg Phe Ser Gly Ser Leu Ile Gly Asp Lys Ala Ala
195 200 205

Leu Thr Ile Val Gly Thr Gln Thr Glu Asp Glu Ala Ile Tyr Phe Cys
210 215 220

Ala Leu Trp Tyr Ser Asp His Trp Val Ile Gly Gly Gly Thr Arg Leu
225 230 235 240

Thr Val Leu Gly

<210> SEQ ID NO 29
<211> LENGTH: 256
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

```
Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Phe
65                  70                  75                  80

Glu Met Asn Ser Leu Gln Ala Asp Asp Thr Ala Met Tyr Tyr Cys Ala
                85                  90                  95

Arg Arg Gly Arg Tyr Pro Tyr Asn Tyr Phe Asp Ala Trp Gly Cys Gly
            100                 105                 110

Thr Thr Val Thr Val Ser Ser Gly Gly Gly Gly Ser Gly Gly Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Gly Gly Thr Arg Leu
225                 230                 235                 240

Thr Val Leu Gly Gly Ser Glu Gln Lys Leu Ile Ser Glu Glu Asp Leu
                245                 250                 255
```

<210> SEQ ID NO 30
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60
```

Ser Arg Leu Asn Ile Tyr Arg Asp Asn Ser Lys Asn Gln Val Phe Phe
65 70 75 80

Glu Met Asn Ser Leu Gln Ala Asp Asp Thr Ala Met Tyr Tyr Cys Ala
85 90 95

Arg Arg Gly Arg Tyr Pro Tyr Asn Tyr Phe Asp Ala Trp Gly Cys Gly
100 105 110

Thr Thr Val Thr Val Ser Ser Gly Gly Gly Gly Ser Gly Gly Gly Gly
115 120 125

Ser Gly Gly Gly Gly Ser Gln Ala Val Val Ile Gln Glu Ser Ala Leu
130 135 140

Thr Thr Ser Pro Gly Glu Thr Val Thr Leu Thr Cys Gly Ser Ser Thr
145 150 155 160

Gly Ala Val Thr Ala Ser Asn Tyr Ala Asn Trp Val Gln Glu Lys Pro
165 170 175

Asp His Cys Phe Thr Gly Leu Ile Gly Gly His Asn Asn Arg Pro Pro
180 185 190

Gly Val Pro Ala Arg Phe Ser Gly Ser Leu Ile Gly Asp Lys Ala Ala
195 200 205

Leu Thr Ile Ala Gly Thr Gln Thr Glu Asp Glu Ala Ile Tyr Phe Cys
210 215 220

Ala Leu Trp Tyr Ser Asp His Trp Val Ile Gly Gly Gly Thr Arg Leu
225 230 235 240

Thr Val Leu Gly

<210> SEQ ID NO 31
<211> LENGTH: 256
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Gln Val Lys Leu Gln Glu Ser Gly Pro Gly Leu Val Gln Pro Ser Gln
1 5 10 15

Ser Leu Ser Ile Thr Cys Thr Val Ser Gly Phe Ser Leu Thr Asp Tyr
20 25 30

Gly Val His Trp Val Arg Gln Ser Pro Gly Lys Ser Leu Glu Trp Leu
35 40 45

Gly Val Ile Trp Ser Gly Gly Gly Thr Ala Tyr Asn Thr Ala Leu Ile
50 55 60

Ser Arg Leu Asn Ile Tyr Lys Asp Asn Ser Lys Asn Gln Val Phe Phe
65 70 75 80

Glu Met Asn Ser Leu Gln Ala Glu Asp Thr Ala Met Tyr Tyr Cys Ala
85 90 95

Arg Arg Gly Ser Tyr Pro Tyr Asn Tyr Phe Asp Ala Trp Gly Cys Gly
100 105 110

Thr Thr Val Thr Val Ser Ser Gly Gly Gly Gly Ser Gly Gly Gly Gly
115 120 125

Ser Gly Gly Gly Gly Ser Gln Ala Val Val Ile Gln Glu Ser Ala Leu
130 135 140

Thr Thr Ser Pro Gly Glu Thr Val Thr Leu Thr Cys Gly Ser Ser Thr
145 150 155 160

Gly Ala Val Thr Ala Ser Asn Tyr Ala Asn Trp Val Gln Glu Lys Pro
165 170 175

Asp His Cys Phe Thr Gly Leu Ile Gly Gly His Asn Asn Arg Pro Pro
180 185 190

Gly Val Pro Ala Arg Phe Ser Gly Ser Leu Ile Gly Asp Lys Ala Ala
195 200 205

Leu Thr Ile Ala Gly Thr Gln Thr Glu Asp Glu Ala Ile Tyr Tyr Cys
210 215 220

Ala Leu Trp Tyr Ser Asp His Trp Val Ile Gly Gly Gly Thr Arg Leu
225 230 235 240

Thr Val Leu Gly Gly Ser Glu Gln Lys Leu Ile Ser Glu Glu Asp Leu
245 250 255

<210> SEQ ID NO 32
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

Gln Val Lys Leu Gln Glu Ser Gly Pro Gly Leu Val Gln Pro Ser Gln
1 5 10 15

Ser Leu Ser Ile Thr Cys Thr Val Ser Gly Phe Ser Leu Thr Asp Tyr
20 25 30

Gly Val His Trp Val Arg Gln Ser Pro Gly Lys Ser Leu Glu Trp Leu
35 40 45

Gly Val Ile Trp Ser Gly Gly Gly Thr Ala Tyr Asn Thr Ala Leu Ile
50 55 60

Ser Arg Leu Asn Ile Tyr Lys Asp Asn Ser Lys Asn Gln Val Phe Phe
65 70 75 80

Glu Met Asn Ser Leu Gln Ala Glu Asp Thr Ala Met Tyr Tyr Cys Ala
85 90 95

Arg Arg Gly Ser Tyr Pro Tyr Asn Tyr Phe Asp Ala Trp Gly Cys Gly
100 105 110

Thr Thr Val Thr Val Ser Ser Gly Gly Gly Gly Ser Gly Gly Gly Gly
115 120 125

Ser Gly Gly Gly Gly Ser Gln Ala Val Val Ile Gln Glu Ser Ala Leu
130 135 140

Thr Thr Ser Pro Gly Glu Thr Val Thr Leu Thr Cys Gly Ser Ser Thr
145 150 155 160

Gly Ala Val Thr Ala Ser Asn Tyr Ala Asn Trp Val Gln Glu Lys Pro
165 170 175

Asp His Cys Phe Thr Gly Leu Ile Gly Gly His Asn Asn Arg Pro Pro
180 185 190

Gly Val Pro Ala Arg Phe Ser Gly Ser Leu Ile Gly Asp Lys Ala Ala
195 200 205

Leu Thr Ile Ala Gly Thr Gln Thr Glu Asp Glu Ala Ile Tyr Tyr Cys
210 215 220

Ala Leu Trp Tyr Ser Asp His Trp Val Ile Gly Gly Gly Thr Arg Leu
225 230 235 240

Thr Val Leu Gly

<210> SEQ ID NO 33
<211> LENGTH: 238
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Arg Gly
            100                 105                 110

Thr Thr Val Thr Val Ser Ser Gly Gly Gly Gly Ser Gly Gly Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Trp Trp Tyr
225                 230                 235

<210> SEQ ID NO 34
<211> LENGTH: 238
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 34

Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Arg Gly
            100                 105                 110

```
Thr Thr Val Thr Val Ser Ser Gly Gly Gly Gly Ser Gly Gly Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Trp Trp Tyr
225                 230                 235


<210> SEQ ID NO 35
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Thr Ala Ala Phe Ile
    50                  55                  60

Ser Arg Leu Asn Ile Tyr Lys Asp Asn Ser Lys Asn Gln Val Phe Phe
65                  70                  75                  80

Glu Met Asn Ser Leu Gln Ala Glu Asp Thr Ala Met Tyr Tyr Cys Ala
                85                  90                  95

Arg Arg Gly Ser Tyr Pro Tyr Asn Tyr Phe Asp Val Trp Gly Cys Gly
            100                 105                 110

Thr Thr Val Thr Val Ser Ser Gly Gly Gly Gly Ser Gly Gly Gly Gly
        115                 120                 125

Ser Gly Gly Gly Gly Ser Gln Ala Val Val Thr Gln Glu Ser Ala Leu
    130                 135                 140

Thr Thr Ser Pro Gly Glu Thr Val Thr Leu Thr Cys Arg Ser Ser Thr
145                 150                 155                 160

Gly Ala Val Thr Thr Ser Asn Tyr Ala Asn Trp Val Gln Glu Lys Pro
                165                 170                 175

Asp His Cys Phe Thr Gly Leu Ile Gly Gly Asn Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asn His Trp Val Phe Gly Gly Gly Thr Arg Leu
225                 230                 235                 240
```

Thr Val Leu Gly Gly Ser Glu Gln Lys Leu Ile Ser Glu Glu Asp Leu
245 250 255

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Gly Gly Gly Gly Ser Gly Gly Gly Gly Ser
1 5 10

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Cys Gly Pro Cys
1

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Gly Gly Gly Gly Ser Gly Gly Gly Gly Ser Leu Pro Glu Thr Gly Gly
1 5 10 15

Ser Gly

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

His Ser Val Asp Val Thr Lys
1 5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Ser Leu Gly Tyr Trp Trp Trp Tyr
1 5

<210> SEQ ID NO 41
<211> LENGTH: 13
<212> TYPE: PRT

<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (8)..(8)
<223> OTHER INFORMATION: Any amino acid

<400> SEQUENCE: 41

Ile Asp Cys Phe Gly Trp Ile Xaa Thr Lys Ala Tyr Phe
1 5 10

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (10)..(10)
<223> OTHER INFORMATION: Any amino acid

<400> SEQUENCE: 42

Arg Gly Leu Val Ile Ala Arg Asp Leu Xaa Thr Thr Val
1 5 10

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

Tyr His Ser Val Asp Val Thr Lys
1 5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Any amino acid

<400> SEQUENCE: 44

Xaa Gln Gln Cys Arg Cys Asn Lys
1 5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 45

Gln Gln Cys Arg Cys Asn Lys
1 5

<210> SEQ ID NO 46

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ile Asp Cys Phe Gly Trp Ile Arg Thr Lys Ala Tyr Phe
1               5                   10


<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Gly Leu Val Ile Ala Arg Asp Leu Ile Thr Thr Val
1               5                   10


<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Gly Gly Gly Ser Gly Gly Gly Gly Ser Gly Gly Gly Gly Ser
1               5                   10                  15
```

ENGINEERED PROTEINS WITH HIGH AFFINITY FOR DOTA CHELATES

RELATED APPLICATIONS

This application claims the benefit of the priority date of U.S. Provisional Application No. 61/156,467, which was filed on Feb. 27, 2009. The content of this provisional application is hereby incorporated by reference in its entirety.

STATEMENT REGARDING FEDERALLY FUNDED RESEARCH

This invention was made with government support under grant number 5-R01-CA101830 awarded by the National Institutes of Health. The government has certain rights in the invention.

SEQUENCE LISTING

The instant application contains a Sequence Listing which has been submitted via EFS-Web and is hereby incorporated by reference in its entirety. The ASCII copy, created on Jun. 14, 2010, is named U2166022.txt and is 83,077 bytes in size.

BACKGROUND

Traditional cancer treatment strategies include chemotherapy, external beam radiation and surgical excision. Chemotherapy is nonspecific and targets all rapidly dividing cells, resulting in undesirable side effects. In addition, tumors can become resistant to chemotherapy. External beam radiation and surgery are only able to target known tumor sites, and will miss undetectable metastases. In the past decade, the development of targeted antibody therapeutics has demonstrated significant improvements in cancer treatment, increasing the number of patient responses to treatment for several types of cancer (Hudson and Souriau, *Nat. Med.* 9:129-134, 2003; Nayeem and Khan, *Curr. Protein Pept. Sci.* 7:165-170, 2006; Tassev and Cheung, *Expert Opin. Biol. Ther.* 9:341-353, 2009; and Weiner et al., *Lancet* 373:1033-1040, 2009).

SUMMARY

The present invention is based, in part, on our discovery of versatile, DOTA-chelate-binding proteins. The proteins can be mono-specific, selectively binding only a metal chelate comprising DOTA (or an active variant of DOTA) and a metal ion. Alternatively, the proteins can be multi-specific, binding both a cellular or molecular target and a metal chelate comprising DOTA (or an active variant thereof) complexed with a metal ion. The target can vary, and suitable targets include cancer antigens, small molecules (e.g., a pharmacologically active or inert compound such as a dye or other label), and proteins expressed by a eukaryotic cell, a prokaryotic cell, or a virus. While we use the term "antigen(s)" when describing certain target molecules, we note that no particular immune response is intended or required. In other words, a cancer antigen need not be one that normally elicits any particular immune response in a subject; any molecule, including a protein or protein-based cancer antigen that is uniquely expressed by a cancerous cell or a tumor cell, can serve as a target for the engineered proteins of the present invention. Similarly, any molecule, including a protein or protein-based molecule uniquely expressed by a pathogen (e.g., a bacterial cell, a fungal cell, a cell of a parasite, or a virus) can serve as a target for an engineered protein of the invention, regardless of the immune response that molecule may or may not elicit from a subject upon infection.

Accordingly, the invention features an engineered protein (e.g., an scFv, other immunoglobulin, or scaffold protein) that specifically binds (a) a metal chelate comprising DOTA, or an active variant thereof, and a metal (without also binding a second target) or (b) both a target molecule and a metal chelate comprising DOTA, or an active variant thereof, and a metal. In either case, the engineered protein can be one that binds the metal chelate with high affinity (e.g., an affinity that is greater than the affinity with which the antibody represented by SEQ ID NO:1 binds the metal chelate). SEQ ID NO:1 is:

```
QVKLQESGPG LVQPSQSLSI TCTVSGFSLT DYGVHWVRQS PGKGLEWLGV
 50

IWSGGGTATY AAFISRLNIY KDNSKNQVFF EMNSLQANDT AMYYCARRGS
100

YPYNYFDVWG QGTTVTVSSG GGGSGGGGSG GGGSQAVVTQ ESALTTSPGE
150

TVTLTCRSST GAVTTSNYAN WVQEKPDHLF TGLIGGNNNR PPGVPARFSG
200

SLIGDKAALT IAGTQTEDEA IYFCALWYSN HWVFGGGFRG RVLG 244
```

Residues 1-119 represent the variable heavy chain of the antibody designated 2D12.5 (Corneillie et al., *J. Am. Chem. Soc.* 125:15039-15048, 2003); residues 120-134 represent a linker; and residues 135-244 represent the variable light chain of 2D12.5.

The engineered protein can be a fusion protein that includes a first amino acid sequence that binds the target and a second amino acid sequence that binds the metal chelate. Alternatively, the engineered protein can be configured as a protein complex (e.g., a covalently bound protein complex, such as a tetrameric antibody or a bispecific antibody, such as the bsAb exemplified below). The first amino acid sequence or the second amino acid sequence can be an immunoglobulin, a scaffolding protein, or an antigen-binding portion of an immunoglobulin or scaffolding protein, and these types of binding proteins can be variously incorporated whether the engineered proteins are configured as a fusion protein, a protein complex, or a combination thereof (e.g., where one or more fusion proteins are complexed with one another or other polypeptides). Where an immunoglobulin or antigen-binding portion thereof is used, it may be a human or humanized immunoglobulin or antigen-binding portion thereof (e.g., of the IgG class).

Immunoglobulins encompass conventionally structured antibodies (e.g., a conventional tetrameric IgG), antigen-binding fragments thereof, and single chain antibodies. Where the engineered protein is, or includes, an scFv that binds a metal chelate, the sequence can be at least or about 70% (e.g., at least or about 75%, 80%, 85%, 90%, 95% or 98%) identical to SEQ ID NO:1, exclusive of the linker at residues 120-134. We specify that the identity can be calculated exclusive of the linker, as many different linker sequences are suitable and can be incorporated where the engineered protein is, or includes, an scFv. The sequence of, or a sequence within, an engineered protein of the present invention can also exhibit a certain percentage of identity to either the light or heavy chain regions of SEQ ID NO:1. For example, an engineered protein of the present invention can include an amino acid sequence that is at least or about 70% (e.g., at least or about 75%, 80%, 85%, 90%, 95% or 98%) identical to either the light chain region or the heavy chain region of SEQ ID NO:1. We may refer to the proteins derived from SEQ ID NO:1 as "affinity matured."

Where the sequence of, or a sequence within, an engineered protein of the present invention is similar to SEQ ID NO:1, certain amino acid residues may remain invariant. For example, amino acid residues that contact the metal chelate can be invariant (e.g., the residues corresponding to one or more of positions 35, 50, 52, 53, 98, 99, 101, 104, 168, 170, and 186 of SEQ ID NO:1 can be invariant). Where mutations are introduced, they can be found less than about 5 Å away from an amino acid residue that contacts the metal chelate, within the second shell, or within the third shell. More specifically, the present engineered proteins can include a mutation at a position corresponding to one or more of the following positions within SEQ ID NO:1: 29, 30, 31, 32, 33, 34, 36, 37, 47, 48, 49, 51, 54, 55, 56, 57, 58, 60, 69, 71, 73, 94, 95, 96, 97, 102, 103, 105, 106, 107, 164, 165, 166, 167, 169, 171, 172, 184, 185, 188, 189, 223, 224, 225, 226, 228, 229, 230, 231, 233, and 234. Alternatively, or in addition, the engineered proteins (e.g., an scFv or scFv-containing protein or protein complex) can include a mutation at a position corresponding to one or more of the following positions within SEQ ID NO:1: 60, 61, 63, 71, 80, 88, 108, 139, 157, 165, 187, 230, and 234. Alternatively, or in addition, the present engineered proteins can include a mutation at a position corresponding to one or more of the following positions within SEQ ID NO:1: 100, 187, and 227.

More specifically, the present engineered proteins can include the sequence of residues 1-244 of mutant C8.2-1 (SEQ ID NO:4); C8.2-2 (SEQ ID NO:6); C8.2-3 (SEQ ID NO:8); C8.2-4 (SEQ ID NO:10); C8.2-5 (SEQ ID NO:12); C8.2-6 (SEQ ID NO:14); C7.3 1 (SEQ ID NO:16); C7.3 2 (SEQ ID NO:18); C7.3 3 (SEQ ID NO:20); C7.3 4 (SEQ ID NO:22); C7.3 5 (SEQ ID NO:24); C7.3 6 (SEQ ID NO:26); C7.3 7 (SEQ ID NO:28); C7.3 8 (SEQ ID NO:30); C7.3 9 (SEQ ID NO:32); or C7.3 10 (SEQ ID NO:34).

In particular embodiments, the engineered proteins can be configured in a bispecific antibody (bsAb) format in which an scFv, optionally stabilized with disulfide bonds, is fused to the C-terminus of one or both of the light chains of an IgG. Thus, the engineered proteins can be IgG-scFv bifunctional (or bispecific) antibodies. Where tetrameric antibodies are included in the present engineered proteins, we may refer to the proteins as "immunoglobulin-like" or "IgG-like" molecules. When expressed in mammalian cells and purified (e.g., by one-step protein A chromatography), the bispecific antibodies can retain the parental affinities of each binding domain, exhibit IgG-like stability, and demonstrate in vivo IgG-like tumor targeting and blood clearance. Our studies have demonstrated that the light chain of an IgG can be extended with an scFv without affecting IgG function and stability. Thus, this format can serve as a standardized platform for the construction of functional bispecific antibodies.

Any of the proteins described herein can include an Fc region, which may prolong the protein's circulating half-life. IgG-like molecules with retained Fc domains may also result in higher tumor uptake than would be observed with smaller fragments. The engineered proteins can also include a mutation that attenuates glycosylation (e.g., a mutation in or adjacent to an N-linked glycosylation site (e.g., position 88 of SEQ ID NO:1) and/or cysteine residues that facilitate the formation of a disulphide bond (e.g., the proteins can be or can include an immunoglobulin (e.g., an scFv) having a cysteine residue in the variable light fragment ($V_L$) and a cysteine residue in the variable heavy fragment ($V_H$) such that a disulfide bond forms between a heavy chain and a light chain of the immunoglobulin). Where the engineered proteins include variants of SEQ ID NO:1, the cysteine residue in $V_L$ can be placed at position 179 and the cysteine residue in $V_H$ can be found at position 111.

The engineered proteins described herein can bind a metal chelate with a Kd of about 1 pM-1 nM (e.g., about 1-10 pM; 1-100 pM; 5-50 pM; 100-500 pM; or 500 pM-1 nM).

The metal ion within the metal chelate bound by the engineered protein can be a trivalent metal cation and can be a radionuclide (e.g., a beta emitter, an alpha emitter, or a low-energy electron emitter) or a paramagnetic metal. More specifically, the metal ion can be actinium, bismuth, copper, europium, gadolinium, gallium, indium (e.g., $^{111}$In), leutinum (e.g., $^{177}$Lu), terbium, or yttrium (e.g., $^{86}$Y).

The metal chelate can be further conjugated to a small molecule, dye, biotin, a polypeptide, or dextran.

We noted above that the engineered proteins of the invention can be fusion proteins in which a first amino acid sequence binds a target and the second amino acid sequence binds a metal chelate. Where the target is a cancer antigen, it can be, without limitation, carcinoembryonic antigen (CEA), A33 antigen, HER-2/neu, MAGE-1, MAGE-3, BAGE, GAGE-1, GAGE-2, MUM-1, CDK4, MUC-1, N-acetylglucosaminyltransferase, p15, gp75, beta-catenin, ErbB2, or cancer antigen 125 (CA-125). Some cancers are associated with viral, bacterial, or parasitic infection, and the target can also be an antigen expressed by the offending virus, bacteria, or parasite.

Active variants of DOTA (e.g., variants conforming to Formula I) are described further below. An "active variant" will exhibit sufficient binding of a metal ion to be useful in place of DOTA.

Also within the scope of the present invention are nucleic acid molecules that encode all or a portion of the engineered proteins described herein (e.g., the nucleic acid may encode the first amino acid sequence or the second amino acid sequence). Also featured are expression vectors (e.g., plasmids) comprising these nucleic acids and host cells including either the nucleic acids per se or expression vectors including them.

Any of the present engineered proteins can be formulated for administration as diagnostic or therapeutic compositions. When configured for therapeutic purposes, the compositions can be used to treat a subject diagnosed as having a proliferative disorder (e.g., cancer or other unwanted cell growth) or an infectious disease (i.e., a disease caused by a pathogen). Accordingly, the present invention features methods comprising a first step of administering to a subject (e.g., a human patient) an effective amount of a pharmaceutical composition including an engineered protein as described herein (e.g., a bispecific antibody targeting a cell proliferating in an undesirable manner or an infectious agent). In a second step, one administers a radionuclide carrying hapten, which is targeted to the virus or cell of interest by virtue of a specific binding site on the engineered protein. The first and second steps can be carried out sequentially, and the second step can be carried out hours to days (e.g., two, three, four, or more days) after the first step. Waiting until the engineered protein has localized to the target before delivering the radiation should produce higher target (e.g., tumor) doses and lower nonspecific doses.

We have also developed a dextran-based blocking agent that reduces DOTA binding to residual engineered proteins (e.g., residual bispecific antibodies) in the blood. When this agent is used, the diagnostic or treatment methods of the present invention include the steps of administering an engineered protein (e.g., a bispecific antibody), administering the dextran-based blocking agent, and administering radiolabeled DOTA. The blocking agent and physiologically acceptable compositions including it are aspects of the present invention. This agent comprises aminodextran conjugated to DOTA. For example, the blocking agent can be a 500 kDa aminodextran conjugated to DOTA. Generally, the resulting compound can include approximately 100-150 (e.g., about 130) DOTA molecules per dextran.

Any of the present engineered proteins can be formulated for administration as diagnostic or pharmaceutical compositions. When configured for therapeutic purposes, the compositions can be used to treat a subject diagnosed as having a proliferative disorder (e.g., cancer or other unwanted cell growth) or an infectious disease. Accordingly, the present invention features methods of administering to a subject an effective amount of a pharmaceutical composition including an engineered protein that specifically binds a target molecule (e.g., a cancer antigen or a moiety expressed by an infectious agent) and DOTA. Thus, the composition specifically targets cells proliferating in an undesirable manner or an infectious agent within the subject. The first amino acid sequence specifically targets the cell or virus, specifically binding an antigen expressed thereon. Because the compositions also include a second amino acid sequence that specifically binds a metal chelate comprising DOTA, subsequently administered radioactive haptens are specifically directed to the targeted cell or virus (to which the engineered protein has already bound). The compositions can be used, for example with beta emitters $^{177}$Lu and $^{90}$Y, targeted MRI with multivalent macromolecular contrast agents containing DOTA-Gd, and neutron capture therapy with $^{157}$Gd.

When configured for diagnostic purposes, the compositions can be used to diagnose a subject suspected of having a proliferative disorder (e.g., cancer or other unwanted cell growth) or an infectious disease. The compositions can be used for external scintigraphy in a variety of ways depending upon the sensitivity required and the location of the suspected lesion. Exemplary methods include pretargeted imaging with positron emission tomography using $^{86}$Y and single photon emission computed tomography using $^{111}$In.

The engineered proteins are also useful in purification schemes, as they can be immobilized (e.g., on a bead or resin used in a column or essentially any solid substrate) and used to specifically bind DOTA chelates.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
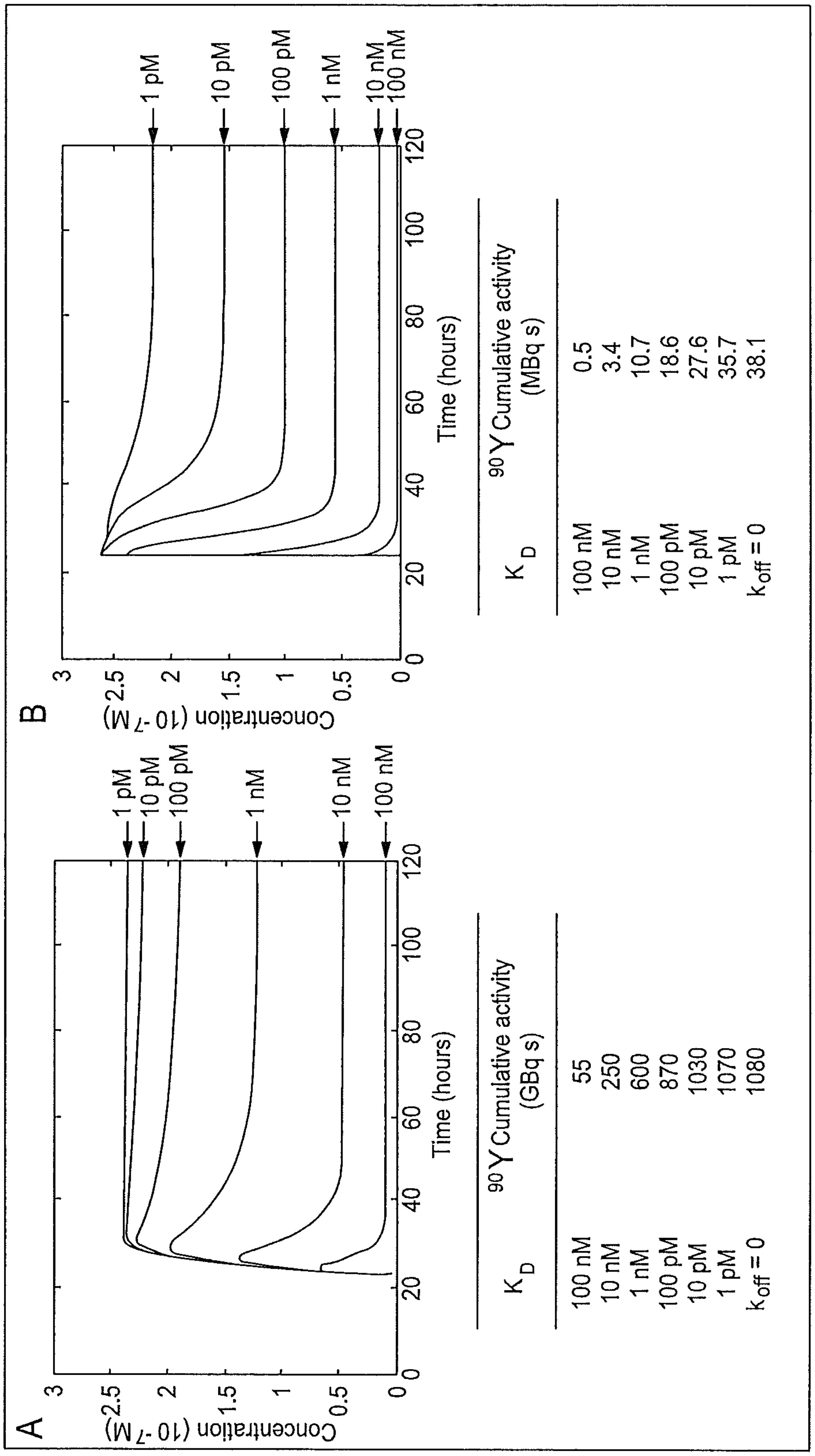
FIG. 1A and FIG. 1B are graphs depicting an analysis of hapten retention in tumors as a function of hapten binding affinity. PRIT simulations were performed assuming a vascularized tumor (FIG. 1A) and a small micrometastasis (FIG. 1B) with human pharmacokinetic parameters. The hapten concentration in the tumor as a function of time was plotted for various dissociation constants (indicated by arrows). The cumulative activity for a $^{90}$Y radionuclide is tabulated for various $K_D$ values and also for a theoretical $k_{off}$ equal to zero. Cumulative activity units are gigabecquerel seconds (GBq s) for the vascularized tumor and megabequerel seconds (MBq s) for micrometastases.

The U.S. Food and Drug Administration approved the first monoclonal antibody for therapeutic use in 1986 and approved the first directly radiolabeled antibody for the treatment of Non-Hodgkin's lymphoma in 2002. In this rapidly expanding field, antibodies to a large variety of targets have now been identified both by the traditional in vivo method of inoculating animals with a target antigen and screening hybridoma clones and by the in vitro use of libraries and screening methods such as phage and yeast display. Directed evolution using molecular biology techniques such as error prone PCR, DNA shuffling, and saturation mutagenesis to generate diversity and selection methods such as phage panning and fluorescence activated cell sorting have been used to affinity mature antibodies to improve binding several fold to several orders of magnitude.

Multi-specific antibodies are designed to contain several binding sites, and thus recognize more than one epitope on the same or multiple antigens. While antibodies have shown success in the clinic for a variety of diseases, multi-specific antibodies may further improve efficacy and introduce additional mechanisms of therapeutic action. Multi-specific antibodies have been engineered to 1) target tumor cells to immune effector cells through antibody dependent cell-mediated cytotoxicity (ADCC), 2) target multiple tumor associated cell surface receptors to both block receptor activation and cross-link the receptors inducing downregulation, and 3) pretarget tumor cells for the delivery of radionuclides, drugs, and prodrugs.

Bispecific antibodies were first synthesized by either co-expressing two antibodies with different specificities through chemical conjugation of two antibodies or fragments thereof or with the hybrid hybridoma technique. Conditions required for chemical conjugation can inactivate, unfold, or aggregate the bispecific antibody. The hybrid hybridoma technique not only produces the desired bispecific antibody but also produces undesired products from mispairing of the two heavy chains and two light chains, and thus requires complex purification schemes. In 1996, Carter and colleagues published a knobs into holes method, where the constant heavy domain 3 (CH3) interface is engineered in one parent antibody to have a large amino acid residue and in the other parent antibody to have a small amino acid residue. These complementary mutations sterically hinder homodimerization and increase the yield of heavy chain heterodimers, thus increasing the yield of the desired bispecific antibody. In the past decade, several different formats of multi-specific antibodies have been synthesized by recombinant and "dock and lock" methods, further improving yields and ease of manufacturing.

Our work concerns (and the present invention includes) mono-specific DOTA-binding proteins as well as engineered proteins, such as multi- or bispecific antibodies, for pretargeted radioimmunotherapy (PRIT) applications. PRIT decouples the pharmacokinetics of antibody targeting and radionuclide delivery, and the technique has been shown to increase efficacy and decrease toxicity in both preclinical (Kraeber-Bodere et al., *J. Nucl. Med.* 47:247-255, 1999; Axworthy et al., *Proc. Natl. Acad. Sci. USA* 97:1802-1807, 2000; Gautherot et al., *J. Nucl. Med.* 41:480-487, 2000; Pagel et al., *Blood* 101:2340-2348, 2003; Sharkey et al., *Cancer Res.* 63:354-363, 2003; Karcay et al., *Clin. Cancer Res.* 11:7879-7885, 2005) and clinical models (Knox et al., *Clin. Cancer Res.* 6:406-414, 2000; Kraeber-Bodere et al., *Clin. Cancer Res.* 5(10 Suppl):3183s-3189s, 2006). In conventional PRIT, the antibody is administered first and allowed to bind to the targeted surface receptor on the cancer cells. Then, a chelatd radionuclide is administered and "captured" by the antibody retained at the site of the cancer. With this two step process, the small radionuclide molecule diffuses rapidly throughout the body and is cleared quickly, significantly reducing the non-specific radiation associated with directly-conjugated antibodies.

The first bispecific antibodies for pretargeting used streptavidin/antibody conjugates and have showed promising proof-of-concept. However, recent pretargeted efforts have moved away from using streptavidin due to its immunogenicity, high kidney uptake, and issues with endogenous biotin. Several bispecific formats that do not utilize streptavidin have been used for pretargeted applications including chemically conjugated Fab and $(Fab)_2$ formats, hybrid hybridoma bispecific antibodies, recombinant diabodies and scFv fusions, and a dock and lock tri-Fab. The present engineered proteins include bispecific antibodies that not only bind simultaneously to both a target (e.g., a cancer antigen) and a small molecule radionuclide, but also retain the Fc binding domain, as this will result in prolonged plasma retention and consequently increased tumor penetration. The Fc binding domain may also result in secondary immune functions that may incur additional therapeutic benefit. We are additionally interested in a bispecific format that does not require construct optimization for each new pair of binding domains. Such a format would provide a platform to construct multiple bispecific antibodies that could be used to explore various tumor antigen targets and capture a variety of small molecule haptens.

We present here, inter alia, an IgG-like bispecific antibody format. This bispecific antibody construct is expressed as an scFv fusion to the C terminus of the light chain of an IgG, creating a bispecific agent with two target-binding sites (e.g., tumor-binding sites) and two hapten capturing sites. We present several bispecific antibodies of this format and show that they simultaneously bind to both their respective cell surface antigen and soluble hapten. The constructs can be produced in mammalian cells, purified by protein A chromatography, and demonstrate retention of parental affinities and stabilities.

The bispecific format was designed as an scFv fusion to the C terminus of an IgG. The heavy chain is the same as that of an IgG1 and was subcloned into the mammalian expression vector gWiz™ (Aldevron cat. #5008) between the PSTI and SALI restriction sites as VH-CH1-CH2-CH3. The constant domains are those of a human IgG1. The light chain is constructed as FLAG-VL-$V_K$-$(G_4S)_2$-scFv-cmyc and subcloned into a separate mammalian expression gWiz™ vector also between the PST1 and SAL1 restriction sites. The bispecific construct was transiently expressed in HEK293 cells (Invitrogen cat. #11625-019). HEK293 cells were grown in flasks on an orbital shaker platform rotating at 140 rpm at 37° C., 5% C02. HEK293 cells were subcultured following the manufacturer's protocols. Cotransfection of heavy and light chain plasmids was performed with polyethyleneimine (PEI) as the transfecting reagent. Briefly, the day before transfection, the HEK293 cells were subcultured to a cell density of 0.5-0.07×$10^6$ cells/mL. About 24 hours later, the cells grew to 1.1-1.5×$10^6$ cells/mL, and were diluted to $10^6$ cells/mL. 20 μg of each purified plasmid (1 mg/mL) was added to 760 μL OptiPRO™ (Invitrogen cat. #12309-019). 80 μL of 1 mg/mL PE1 was added to 720 μL OptiPRO™. Both OptiPRO™ solutions were incubated at room temperature for 5 minutes. The DNA/OptiPRO™ solution was added to the PEI/OptiPRO™ solution and incubated for an additional 10 minutes at room temperature and then added dropwise to 40 mL HEK293 culture at $10^6$ cells/mL. The supernatant was collected 6-8 days after transfection. Antibodies were purified by protein A chromatography (Pierce cat. #22811) following the manufacturer's instructions.

Engineered proteins: We tend to use the term "protein" to refer to longer or larger amino acid polymers and multi-chain or multi-unit proteinacious molecules, and we tend to use the term "polypeptide" to refer to shorter sequences or to a chain of amino acid residues within a larger molecule (e.g., within a fusion protein) or complex. Both terms, however, are meant to describe an entity of two or more subunit amino acids, amino acid analogs, or other peptidomimetics, regardless of post-translational modification (e.g., amidation, phosphorylation or glycosylation). The subunits can be linked by peptide bonds or other bonds such as, for example, ester or ether bonds. The terms "amino acid" and "amino acid residue" refer to natural and/or unnatural or synthetic amino acids, which may be D- or L-form optical isomers.

Immunoglobulins. The first and/or second polypeptides within the engineered proteins may be, or may be a part of, an immunoglobulin. The immunoglobulins can assume various configurations and encompass proteins consisting of one or more polypeptides substantially encoded by immunoglobulin genes. We may use the term "immunoglobulin" synonymously with "antibody."

An immunoglobulin can be a tetramer (e.g., an antibody having two heavy chains and two light chains) or a single-chain immunoglobulin, and any of the polypeptides in the tetramer or the single polypeptide of the single chain antibody may be used as the first and/or second polypeptide of the present engineered proteins. Accordingly, the first and/or second polypeptide can be one of the two heavy chains or heavy chain variable regions or one of the two light chains or light chain variable regions. The VHC and VLC regions are further subdivided into regions of hypervariability, termed "complementarity determining regions" (CDRs), interspersed with the more conserved framework regions (FRs). The extent of the FRs and CDRs has been defined (see, Kabat, E. A., et al. *Sequences of Proteins of Immunological Interest*, Fifth Edition, U.S. Department of Health and Human Services, NIH Publication No. 91-3242, 1991, and Chothia, et al., *J. Mol. Biol.* 196:901-917, 1987, which are incorporated herein by reference).

The $V_H$ or $V_L$ chain of an immunoglobulin can further include all or part of a heavy or light chain constant region. For example, the present first and second polypeptides can be within an immunoglobulin tetramer of two heavy immunoglobulin chains and two light immunoglobulin chains, wherein the heavy and light immunoglobulin chains are interconnected by, e.g., disulfide bonds. The heavy chain constant region includes three domains: CH1, CH2 and CH3. The light chain constant region is comprised of one domain: CL. The variable regions of the heavy and light chains contain a binding domain that interacts with an antigen. The polypeptides may be those of intact immunoglobulins of types IgA, IgG, IgE, IgD, IgM (as well as subtypes thereof (e.g., $IgG_1$, $IgG_2$, $IgG_3$, and $IgG_4$)), and the light chains of the immunoglobulin may be of types kappa or lambda. The recognized human immunoglobulin genes include the kappa, lambda, alpha ($IgA_1$ and $IgA_2$), gamma ($IgG_1$, $IgG_2$, $IgG_3$, $IgG_4$), delta, epsilon, and mu constant region genes, as well as the myriad immunoglobulin variable region genes.

Polypeptides within the engineered proteins of the present invention may include CDRs from a human or non-human source. The framework of the immunoglobulin can be human, humanized, or non-human (e.g., a murine framework modified to decrease antigenicity in humans), or a synthetic framework (e.g., a consensus sequence). Humanized immunoglobulins are those in which the framework residues correspond to human germline sequences and the CDRs result from V(D)J recombination and somatic mutations. However, humanized immunoglobulins may also comprise amino acid residues not encoded in human germline immunoglobulin nucleic acid sequences (e.g., mutations introduced by random or site-specific mutagenesis ex vivo). It has been demonstrated that in vivo somatic mutation of human variable genes results in mutation of framework residues (see *Nat. Immunol.* 2:537, 2001). Such an antibody would be termed "human" given its source, despite the framework mutations. Mouse antibody variable domains also contain somatic mutations in framework residues (See *Sem. Immunol.* 8:159, 1996). Consequently, transgenic mice containing the human Ig locus produce immunoglobulins that are commonly referred to as "fully human," even though they possess an average of 4.5 framework mutations (*Nature Genet.* 15:146-56, 1997). Accepted usage therefore indicates that an antibody variable domain gene based on germline sequence but possessing framework mutations introduced by, for example, an in vivo somatic mutational process is termed "human." As noted above, the present engineered proteins encompass those that specifically bind a cellular target and a activating Fc receptor even where those proteins include mutations (e.g., mutations within the FR) and fragments or other variants thereof (e.g., single chain antibodies that include the VLC and VHC of a multimeric human antibody).

The term "antigen-binding portion" of an immunoglobulin or antibody (or simply "antibody portion," or "portion"), as used herein, refers to a portion of an immunoglobulin that specifically binds to a cellular target. An antigen-binding portion of an immunoglobulin is therefore a molecule in which one or more immunoglobulin chains are not full length, but which specifically binds to a cellular target. Examples of antigen-binding portions or fragments that can be used in the present proteins include: (i) an Fab fragment, a monovalent fragment consisting of the VLC, VHC, CL and CH1 domains; (ii) a $F(ab')_2$ fragment, a bivalent fragment comprising two Fab fragments linked by a disulfide bridge at the hinge region; (iii) a Fd fragment consisting of the VHC and CH1 domains; (iv) a Fv fragment consisting of the VLC and VHC domains of a single arm of an antibody, (v) a dAb fragment (Ward et al., *Nature* 341:544-546, 1989), which consists of a VHC domain; and (vi) an isolated complementarity determining region (CDR) having sufficient framework to specifically bind, e.g., an antigen binding portion of a variable region. An antigen-binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFv); see e.g., Bird et al., *Science* 242:423-426, 1988; and Huston et al., *Proc. Natl. Acad. Sci. USA* 85:5879-5883, 1988).

These antibody portions are obtained using conventional techniques known to one of ordinary skill in the art, and the portions are screened for utility in the same manner as intact antibodies. An Fab fragment can result from cleavage of a tetrameric antibody with papain; Fab' and F(ab')2 fragments can be generated by cleavage with pepsin.

In summary, single chain immunoglobulins, and chimeric, humanized or CDR-grafted immunoglobulins, including those having polypeptides derived from different species, can be incorporated into the engineered proteins.

The various portions of these immunoglobulins can be joined together chemically by conventional techniques, or can be prepared as contiguous polypeptides using genetic engineering techniques. For example, nucleic acids encoding a chimeric or humanized chain can be expressed to produce a contiguous polypeptide. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger et al., WO 86/01533; Neuberger et al., European Patent No. 0,194,276 B1; Winter, U.S. Pat. No. 5,225,539; and Winter, European Patent No. 0,239,400 B1. See also, Newman et al., *BioTechnology* 10:1455-1460, 1992, regarding CDR-graft antibody, and Ladner et al., U.S. Pat. No. 4,946,778 and Bird et al., *Science* 242:423-426, 1988, regarding single chain antibodies.

Nucleic acid (e.g., DNA) sequences coding for any of the polypeptides within the present engineered proteins are also within the scope of the present invention as are methods of making the engineered proteins. For example, variable regions can be constructed using PCR mutagenesis methods to alter DNA sequences encoding an immunoglobulin chain, e.g., using methods employed to generate humanized immunoglobulins (see e.g., Kanunan et al., *Nucl. Acids Res.* 17:5404, 1989; Sato et al., *Cancer Research* 53: 851-856, 1993; Daugherty et al., *Nucleic Acids Res.* 19(9):2471-2476, 1991; and Lewis and Crowe, *Gene* 101: 297-302, 1991). Using these or other suitable methods, variants can also be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

Other suitable methods of producing or isolating immunoglobulins that specifically recognize a cellular target include, for example, methods that rely upon immunization of transgenic animals (e.g., mice) capable of producing a full repertoire of human antibodies (see e.g., Jakobovits et al., *Proc. Natl. Acad. Sci. USA* 90:2551-2555, 1993; Jakobovits et al., *Nature* 362:255-258, 1993; Lonberg et al., U.S. Pat. No. 5,545,806; Surani et al., U.S. Pat. No. 5,545,807). These U.S. patents are incorporated by reference herein.

The binding affinities of an engineered protein of the present invention (e.g., an immunoglobulin, an immunoglobulin-like protein, or of any of the other types of binding entities described herein as useful in the engineered proteins) can be readily determined by one of ordinary skill in the art, for example, by Scatchard analysis (Scatchard, *Ann. NY Acad, Sci.* 51:660-672, 1949).

The engineered proteins can bind a metal chelate with an affinity of, for example, $10^{-4}$M or less, $10^{-7}$M or less, $10^{-9}$M or less or with subnanomolar affinity (0.9, 0.8, 0.7, 0.6, 0.5, 0.4, 0.3, 0.2, 0.1 nM or even less). In one embodiment, the engineered proteins have an affinity for a metal chelate (i.e., a moiety comprising DOTA, or an active variant of DOTA, and a chelated metal ion) that is greater than the affinity with which the immunoglobulin (an scFv) represented by SEQ ID NO:1 binds the metal chelate. The affinities of the engineered protein and/or the scFv of SEQ ID NO:1 can be determined by any method known in the art for measuring affinity (e.g., flow cytometry) and, where affinities of two proteins are being compared, the respective affinities can be determined under the same or comparable conditions (e.g., at the same temperature (e.g., 25° C. or 37° C.)). See, for example, the article by Gai and Wittrup (*Curr. Opin. Struct. Biol.* 17:467-473, 2007), particularly FIG. 3, which compares dissociation constants determined by yeast surface display and other methods, including affinities measured in a Biacore™ system. For the engineered proteins of the invention, the affinity (e.g., the affinity for a metal chelate) is preferably in the range of about 1 nM to about 1 pM, for example, about 900 pM, 800 pM, 700 pM, 600 pM, 500 pM, 400 pM, 350 pM, 300 pM, 250 pM, 200 pM, 150 pM, 100 pM, 50 pM, 40 pM, 30 pM, 20 pM, 10, pM, 8 pM, 5 pM. 2.5 pM, 2 pM, or 1 pM. More specifically, the affinity can be about 8.2 pM.

As noted, where the present engineered proteins are derived from SEQ ID NO:1 or include a sequence derived from SEQ ID NO:1 (i.e., where the engineered proteins are, or include, a sequence that exhibits a high degree of identity to SEQ ID NO:1 (e.g., at least 70% identity), the protein may be invariant at one or more of the contact residues and variant (e.g., by virtue of including a substitution mutation) at one or more of the residues within the second or third shells. These positions are noted below, with respect to SEQ ID NO:1 and the Kabat numbering system. The corresponding sequence position and the residue at that position may be shown in parenthesis.

Contact Residues (<5 Angstroms)

Light chain: L32 (is position 34; Y), L34 (36; N), L50 (52; G), L51 (53; N), L91 (93; W), L96 (98; W).

Heavy chain: H35 (35; H), H50 (50; V), H52 (52; W), H53 (53; S), H95 (98; R), H96 (99; G), H97 (100; S), H98 (101; Y), H100A (104; N).

2nd Shell Residues (<5 Angstroms from Contact Residues)

Light chain: L28 (is 30; T), L29 (is 31; T), L30 (is 32; S), L31 (is 33; N), L33 (is 35; A), L35 (is 37; W), L36 (is 38; V), L48 (is 50; I), L49 (is 51; G), L52 (is 54; N), L53 (is 55; N), L87 (is 89; F), L88 (is 90; C), L89 (is 91; A), L90 (is 92; L), L92 (is 94; Y), L93 (is 95; S), L94 (is 96; N), L95 (is 97; H), L97 (is 99; V), L98 (is 100; F).

Heavy chain: H29 (is 29; L), H30 (is 30; T), H31 (is 31; D), H32 (is 32; Y), H33 (is 33; G), H34 (is 34; V), H36 (is 36; W), H37 (is 37; V), H47 (is 47; W), H48 (is 48; L), H49 (is 49; G), H51 (is 51; I), H54 (is 54; G), H55 (is 55; G), H56 (is 56; G), H57 (is 57; T), H58 (is 58; A), H60 (is 60; T), H69 (is 69; I), H71 (is 71; K), H73 (is 73; N), H91 (is 94; Y), H92 (is 95; C), H93 (is 96; A), H94 (is 97; R), H99 (is 102; P), H100 (is 103; Y), H100B (is 105; Y), H100C (is 106; F), H101 (is 107; D).

3rd Shell Residues (<5 Angstroms from 2nd Shell Residues)

Light chain: L1, L2, L3, L4, L6, L21, L22, L23, L24, L25, L26, L27, L27B, L27C, L37, L38, L42, L44, L45, L46, L47, L54, L55, L56, L62, L63, L64, L65, L66, L71, L72, L73, L85, L86, L99, L100, L101.

Heavy chain: H2, H4, H6, H20, H21, H22, H24, H26, H27, H28, H38, H39, H44, H45, H46, H59, H61, H62, H63, H64, H67, H68, H70, H72, H74, H75, H76, H77, H78, H79, H80, H89, H90, H102, H103, H104, H105, H106, H107.

The engineered proteins (e.g., immunoglobulins, immunoglobulin-like molecules, and other scaffold proteins) may be modified to reduce or abolish glycosylation. A protein (e.g., an immunoglobulin) that lacks glycosylation may be an immunoglobulin that is not glycosylated at all; that is not fully glycosylated; or that is atypically glycosylated (i.e., the glycosylation pattern for the mutant differs from the glycosylation pattern of the corresponding wild type immunoglobulin). The IgG polypeptides can include one or more (e.g., 1, 2, or 3 or more) mutations that attenuate glycosylation, i.e., mutations that result in the an IgG CH2 domain that lacks glycosylation, or is not fully glycosylated or is atypicially glycosylated. The mutations can be in or adjacent to an N-linked glycosylation site, for example, within the C'/E loop of the CH2 domain. Mutations at positions 297, 298 and 299 of human IgG1 are two examples of such mutations. The mutant IgGs can also include mutations in the CH2 domain outside the C'/E loop, for example, at position 290, e.g., K290N, K290E, or at position 326, e.g., K326E.

In one embodiment, the present invention features a bispecific antibody that includes a first amino acid sequence that specifically binds a target molecule and a second amino acid sequence that specifically binds a metal chelate comprising DOTA or an active variant thereof (the chelate carrying a metal ion, such as a radionuclide). The first amino acid sequence can include a a variable heavy chain and/or a variable light chain of an immunoglobulin, and can have the structure of a conventional tetrameric IgG. The second amino acid sequence can be, or can include, an scFv. The scFv can be at least or about 70% (e.g., at least 75%, 80%, 85%, 90%, or 95%) identical to SEQ ID NO:1, exclusive of the linker at residues 120-134. The scFv within the bispecific antibody can specifically bind a metal chelate comprising DOTA with a Kd of about 1 pM-1 nM. As in other embodiments, the target molecule can be a cancer antigen or an antigen expressed by a virus, bacterial cell, or parasite. Nucleic acids encoding these bispecific antibodies are within the scope of the invention, as are expression vectors including sequences that encode them, and host cells that contain them. The bispecific antibodies can be used in the methods of treatment described herein, the purification methods described herein, and in methods for the manufacture of a medicament (e.g., for the treatment of cancer or an infectious disease).

Scaffold proteins: As an alternative to, or in addition to, immunoglobulins, the engineered proteins of the present invention can include scaffold proteins. These proteins are those that share certain structural features with immunoglobulins, for example, a β-sheet secondary structure. Examples of useful scaffold proteins include the following.

Fibronectin domains: The engineered proteins can include a fibronectin type III (Fn3) domain (e.g., the tenth type III domain of human Fn3). Fn3 is a small (~10 kDa), stable β-sandwich with an immunoglobulin-like fold; three exposed loops termed BC, DE, and FG are structurally analogous to antibody complementarity-determining regions (CDRs). Exemplary sequences of human fibronectin include NP_002017.1 G1:16933542; the tenth type III domain includes a region extending from about amino acids 1447 to about 1550.

Fn3 polypeptides, Fn3 polypeptide monobodies, and methods of making these compositions are described in U.S. Pat. No. 5,153,661, which is hereby incorporated by reference in its entirety. The polypeptides of U.S. Pat. No. 5,153, 661 can be used in the present engineered proteins or modified to alter their binding specificity and used in the present engineered proteins. Proteins that generally make use of a scaffold derived from Fn3 are also disclosed in U.S. Pat. No. 7,115,396, which is incorporated herein by reference, and may be used to make the first and/or second polypeptides within the present engineered polypeptides.

Other constructs relying on the fibronectin type III domain include, for example, iMabs or "monobodies" described, for example, in Koide and Koide (Methods in Molecular Biology, vol 352: *Protein Engineering Protocols*, (2007) p. 95-109) and Adnectins or Trinectins, which are selected to include two, three or four loops that connect the strands on one end of the beta-sandwich, similar to the CDRs of an antibody.

Other members of this class include: human cytotoxic T-lymphocyte associated protein 4 (CTLA-4) which comprises CDR-like loops similar to antibodies that are permissive to loop replacements; neocarzinostatin, an enediyne-binding chromoprotein isolated from *Streptomyces carzinostaticus* which consists of seven β-strands in two sheets forming a β-sandwich, a topology similar to the immunoglobulin fold; Carbohydrate binding module 4-2, derived from the *Rhodothermus marinus* xylanase Xyn10A, which has a β-sandwich structure formed by 11 strands and contains no disulfide bonds; tendamistat, a 74-residue inhibitor of α-amylase from *Streptomyces tendae*, which includes an α-amylase-binding loop 1 permissive to randomization; and the β-barrel green fluorescent protein (GFP).

Nonimmunoglobulin scaffolds: Nonimmunoglobulin-like scaffolds can also be used in the engineered proteins of the invention. Examples of useful scaffolds that can be engineered to selectively bind a cellular target or an activating Fc receptor include the following general classes of polypeptides.

Scaffolds exhibiting a contiguous hypervariable loop region: Lipocalins are 160- to 180-residue polypeptides involved in storage or transport of hydrophobic and/or chemically sensitive organic compounds. They consist of a central β-barrel of eight anti-parallel β-strands, which support a set of four hypervariable loops that form the ligand binding site. The four hypervariable loops connect the β-strands in a pairwise fashion at the open end of this central folding motif. The position of the mutant amino acids depends upon the nature of the target. Typically, where a lipocalin is employed, it may include one or more mutations in the cavity, the loops, or both. Exemplary members of the lipocalin family include apolipoprotein D (ApoD) and bovine heart fatty acid-binding protein (FABP).

Single peptide loops displayed on a carrier protein: Kunitz-type inhibitors of serine proteases are a group of small, irregular protease inhibitors with few secondary structures exposing a more or less extended peptide stretch with varying sequence. Exemplary Kunitz type inhibitors of serine proteases include beef pancreas trypsin inhibitor, human lipoprotein associated coagulation inhibitor D1, human inter-α trypsin inhibitor, human pancreatic secretory trypsin inhibitor (PSTI), Alzheimer's amyloid β-protein precursor inhibitor (APPI), the leech-derived trypsin inhibitor (LTDI), the mustard trypsin inhibitor II (MTI II) and the periplasmic *E. coli* protease inhibitor ecotin.

Thioredoixins are small, highly soluble and structurally robost enzymes involved in the cytosolic thiol/disulfide equilibrium of *E. coli*. The short active site sequence of Cys-Gly-Pro-Cys forms a tight disulfide bridged and solvent accessible loop in the oxidized state and permits the insertion of long peptide stretches. Peptide aptamers have been selected from corresponding random loop libraries.

The "knottin family" comprises small, 25- to 35-residue proteins, some of which also function as protease inhibitors. They include conserved disulfide bonds, leading to a characteristic knotted topology, and interspersed variable peptide loops. They typically contain a small triple stranded antiparallel b-sheet and cysteine-knot motif that arises from three interlocking disulfide bridges. Knottin scaffolds are also known as miniproteins or microbodies. Examples of useful knottins include the trypsin inhibitor from the squirting cucumber *Ecballium elaterium* (EETI-II), the C-terminal cellulose-binding domain (CBD) of cellobiohydrolase I from the fungus *Trichoderma reesei.*

Other examples of useful scaffold proteins in this class include insect defensin A, which forms an α-helix and two β-strands, has two loop regions with tolerance for substitutions, and is stabilized by two disulfide bridges; the PDZ domain, a protein-recognition module involved in signaling networks, which contains three α-helices and five β-strands; scorpion toxins, for example, charybdotoxin from *Leiurus quinquestriatus hebraeus*, which includes a 37-residue motif consisting of an anti-parallel triple-stranded β-sheet, a short α-helix, and three stabilizing disulfide bonds; the plant homeodomain (PHD) finger protein a small protein with a well-structured core that contains two zinc ions, no disulfide bonds and two variable and flexible loops that seem to be tolerant to mutagenesis, expansion, and loop grafting; and TEM-1 β-lactamase a larger protein (263 residues) that has a protein backbone consisting of numerous α-helices and β-sheets, and a disulfide bond.

Interfaces resting on secondary structures; α-helical frameworks and β-sheets: The Z domain, one of the five stable three-α-helix bundle domains from the immunoglobulin Fc-binding region of staphylococcal protein A, is highly soluble, proteolytically and thermally stable, and does not contain disulfide bonds. Thirteen surface residues involved in Fc-binding have been randomized to generate so-called affibodies; the affinity and avidity of affibodies has been further increased by α-helix shuffling and multimerization.

Ankyrin repeat domains consist of repetitive structural units of 33 residues comprising a β-turn followed by two anti-parallel α-helices and a loop linking up to the turn of the next repeat. Designed ankyrin repeat proteins (DARPins) with up to four repeats between N- and C-terminal capping repeats can be used to generate a polypeptide that selectively binds an activating FcR. Mutations can be introduced into a number of regions, for example, the β-turn, α-helix, and loop region, representing the binding surface under natural conditions.

Other proteins that fall within this class include the consensus repeat sequence from leucine-rich repeat proteins (mammalian ribonuclease inhibitor family), and the Affilins, engineered proteins comprising two different protein scaffolds: human γ-crystallin, a durable protein from the eye lens, and human ubiquitin, a small protein normally involved in intracellular protein degradation. Also included in this class are the immunity proteins, exemplified by the all-α-coil scaffold of *E. coli* colicin E7 immunity protein (ImmE7), an 87-residue protein that contains no cysteines and folds into a four-helix bundle topology (α-helices I-IV). α-Helices I and III are followed by two loops; Cytochrome b562 a four-helix bundle protein with two loops connecting the α-helical framework; peptide α2p8, a 38-amino acid peptide, comprising an α-helical hairpin that is derived from the two N-terminal helices of the human p8MTCP1 protein (a small 8-kDa protein encoded by the human oncogene MTCP1).

Oligomeric domain structures: This class of proteins includes engineered multidomain proteins that form complexes of oligomeric structure and multiple interactions. One example of this class are the avimers, also known as maxibodies, artificial multidomain proteins derived from the human A-domains as they occur in the low-density lipoprotein receptor (LDLR). The scaffold comprises 35 amino acids, two-thirds of which may be variable, and the confirmation is determined by three disulfide bonds and a complexed calcium ion. Another example in this class is the Trinectins, homotrimeric proteins that include a C-type lectin domain (CTLD) and coiled coil trimerization module. The CTLDs share a conserved structural core, which supports a loop that forms the sugar binding site.

Targets

The engineered proteins of the present invention are useful in sorting and/or purification techniques and as therapeutic proteins. The proteins can specifically bind to cellular targets implicated in a wide range of diseases or disorders (e.g., cancer). For example, the proteins can bind cell surface proteins and other types of antigens and, by virtue of binding the cell surface, can bind a cell per se. The target can be a protein or other molecule expressed by a virus, or it can be a cellular target. For example, the target can be a protein or other type of molecule expressed by a cell that is proliferating undesirably (e.g., a cancerous cell in a patient) or by a bacterial cell or a cell within a parasite. Where the target is expressed by a patient's own cells, it may be a "cancer antigen" or a "tumor-associated antigen" (TAA), including a polypeptide-, carbohydrate- or lipid-based antigen. Preferably, the cancer antigen or TAA will differ qualitatively from any counterpart expressed in normal cells (i.e., cells unaffected by the cancer and non-proliferating or proliferating normally).

Examples of cancers that can be treated with the engineered proteins include, without limitation, hematological cancers such as leukemias and lymphomas (e.g., Burkitt lymphoma, non-Hodgkin lymphoma, Hodgkin lymphoma, and acute T cell leukemia) neurological tumors such as brain tumors, astrocytomas or glioblastomas, melanomas, breast cancer, lung cancer, head and neck cancer, gastrointestinal tumors such as stomach, colon or colorectal cancer, liver cancer, pancreatic cancer, genitourinary tumors such ovarian cancer, vaginal cancer, vulval cancer, bladder cancer, testicular cancer, prostate cancer, or penile cancer, bone tumors, and vascular tumors. Examples of specific TAAs include, without limitation, A33 antigen, HER-2/neu, MAGE-1, MAGE-3, BAGE, GAGE-1, GAGE-2, MUM-1, CDK4, MUC-1, N-acetylglucosaminyltransferase, p15, gp75, beta-catenin, ErbB2, or cancer antigen 125 (CA-125), carcinoembryonic antigen (CEA), RAGE, MART (melanoma antigen), MUC (mucin) (e.g., MUC-1, MUC-2, etc.), tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, p53, lung resistance protein (LRP) Bc1-2, prostate specific antigen (PSA), and Ki-67. The "first" amino acid sequence as described herein can be one that specifically binds any of these molecules.

The target can also be a molecule (e.g., a protein antigen) expressed by a virus, bacterium, or parasite. Each of these pathogens can cause disease, and in some instances the disease can be cancer. For example, the hepatitis B virus and the hepatitis C virus are associated with hepatocellular cancer; the human papillomavirus (particularly certain types expressing an E6 or E7 antigen) is associated with cervical, vaginal, vulvar, propharyngeal, anal, and penile cancers; the herpes simplex virus is associated with cervical cancer; Epstein-Barr virus is associated with Burkitt lymphoma, Hodgkin and non-Hodgkin lymphoma, and nasopharyngeal cancers; human T cell lymphotropic virus 1 (HTLV1) is associated with acute T cell leukemia; the bacteria *Helicobacter pylori* is associated with stomach cancer; the parasite schistosomes (*Schistosoma hematobium*) is associated with bladder cancer; and liver flukes (*Opisthorchis viverrini*) is associated with cholangiocarcinomas. Antigens expressed by these pathogens can be targeted with the first amino acid sequence of the present engineered proteins, with the second amino acid sequence subsequently binding a DOTA chelate-radiometal complex aimed at the destruction of the target cell.

Metal Chelates

Figure 2:
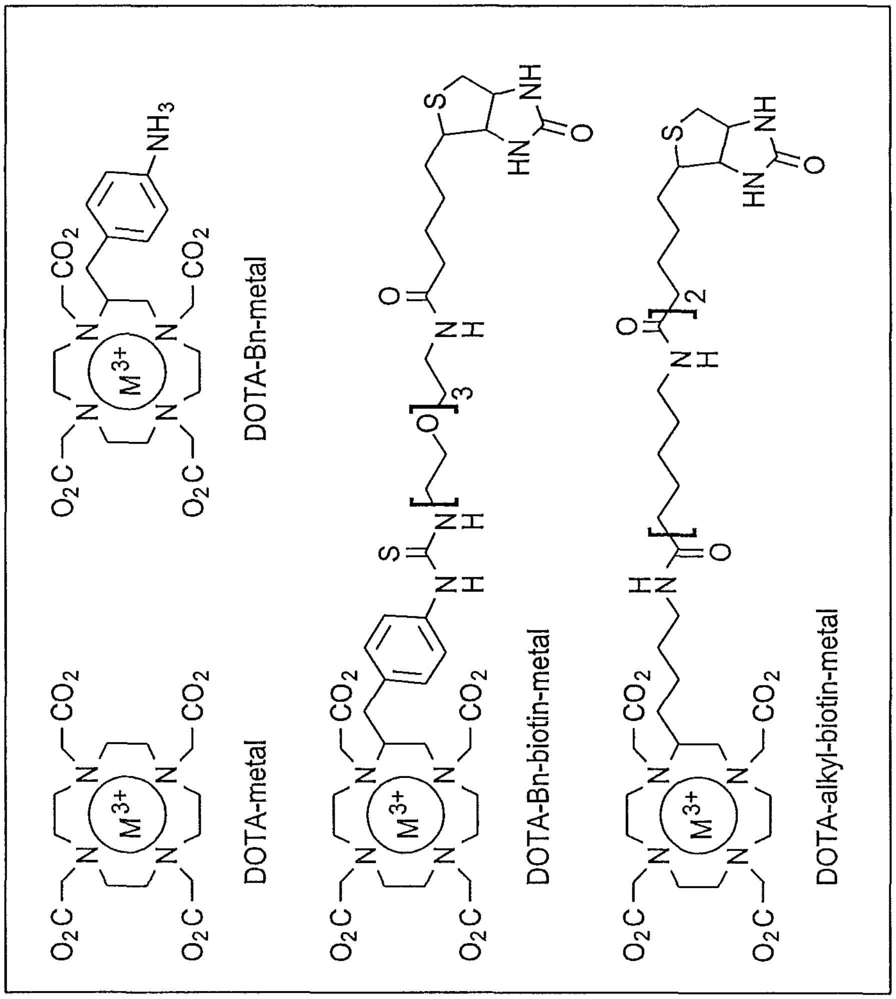
FIG. 2 depicts chemical structures of the DOTA variants used with trivalent metal cations.

The engineered proteins of the invention bind to metal chelates that include DOTA (1,4,7,10-tetraazacyclododecane-N,N',N'',N'''-tetraacetic acid) or an active variant of DOTA and a metal ion (including radionuclides). DOTA is a macrocyclic chelating agent that forms stable complexes with metals that are essentially irreversible under physiological conditions. DOTA has a molecular weight of 405 Daltons, diffuses very rapidly, and exhibits rapid renal clearance. DOTA and examples of active DOTA variants are shown in FIG. 2. A variant of DOTA that has a structure that differs to a certain limited extent from the structure of DOTA and that retains the ability to function (e.g., retains sufficient activity to be used for one or more of the purposes described herein) is an active variant of DOTA. These active variants include compounds of Formula I:

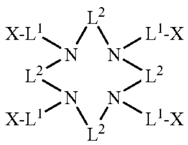

I or a pharmaceutically acceptable salt thereof; wherein:

each X is independently selected from carboxy, —C(═O)NHR$^d$, —P(═O)(OH)(OR$^d$), —S(═O)OH, —S(═O)$_2$OH, —SH, —OH, —OC(═O)NHR$^d$, —OC(═S)NHR$^d$, —NHC(═0)NR$^e$R$^f$, —NHC(═S)NR$^e$R$^f$, —NR$^e$C(═O)NHR$^f$, and —NR$^e$C(═S)NHR$^f$;

each L$^1$ is, independently, $C_{1-6}$ alkylene, $C_{1-6}$ alkenylene, or $C_{1-6}$ alkynylene, each of which is optionally substituted by 1, 2, or 3 groups independently selected from halogen, cyano, nitro, hydroxyl, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, amino, $C_{1-4}$ alkylamino, di-$C_{1-4}$-alkylamino, $C_{1-4}$ alkylcarbonyl, carboxy, $C_{1-4}$ alkoxycarbonyl, $C_{1-4}$-alkylcarbonylamino, di-$C_{1-4}$-alkylcarbonylamino, $C_{1-4}$-alkoxycarbonylamino, $C_{1-4}$-alkoxycarbonyl-($C_{1-4}$ alkyl)amino, carbamyl, $C_{1-4}$ alkylcarbamyl, and di-$C_{1-4}$-alkylcarbamyl;

each L$^2$ is independently, $C_{2-4}$ straight chain alkylene, which is optionally substituted by an independently selected R$^1$ group and which is optionally substituted by 1, 2, 3, or 4 groups independently selected from $C_{1-4}$ alkyl and $C_{1-4}$ haloalkyl;

each R$^1$ is independently selected from H, -D$^1$-D$^2$-D$^3$, halogen, cyano, nitro, hydroxyl, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, amino, $C_{1-6}$ alkylamino, di-$C_{1-6}$-alkylamino, $C_{1-4}$ alkylcarbonyl, carboxy, $C_{1-6}$ alkoxycarbonyl, $C_{1-6}$-alkylcarbonylamino, di-$C_{1-6}$-alkylcarbonylamino, $C_{1-6}$-alkoxycarbonylamino, $C_{1-6}$-alkoxycarbonyl-($C_{1-6}$ alkyl)amino, carbamyl, $C_{1-6}$ alkylcarbamyl, and di-$C_{1-6}$-alkylcarbamyl;

each D$^1$ is independently selected from $C_{6-10}$ aryl-$C_{1-4}$-alkyl, $C_{1-9}$ heteroaryl-$C_{1-4}$-alkyl, $C_{3-10}$-cycloalkyl-$C_{1-4}$-alkyl, $C_{2-9}$ heterocycloalkyl-$C_{1-4}$-alkyl, $C_{1-8}$ alkylene, $C_{1-8}$ alkenylene, and $C_{1-8}$ alkynylene; wherein said $C_{1-8}$ alkylene, $C_{1-8}$ alkenylene, and $C_{1-8}$ alkynylene are each optionally substituted by 1, 2, 3, or 4 independently selected R$^4$ groups; and wherein said $C_{6-10}$-aryl-$C_{1-4}$-alkyl, $C_{1-9}$ heteroaryl-$C_{1-4}$-alkyl, $C_{3-10}$ cycloalkyl-$C_{1-4}$-alkyl, and $C_{2-9}$ heterocycloalkyl-$C_{1-4}$-alkyl are each optionally substituted by 1, 2, 3, or 4 independently selected R$^5$ groups;

each D$^2$ is independently absent or $C_{1-20}$ straight chain alkylene, wherein from 1 to 6 non-adjacent methylene groups of said $C_{1-20}$ straight chain alkylene are each optionally replaced by an independently selected-D$^4$-moiety, provided that at least one methylene unit in said $C_{1-20}$ straight chain alkylene is not optionally replaced by a -D$^4$-moiety; wherein said $C_{1-20}$ straight chain alkylene is optionally substituted by one or more groups independently selected from halogen, cyano, nitro, hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, di-$C_{1-4}$-alkylamino, $C_{1-4}$ alkylcarbonyl, carboxy, $C_{1-4}$ alkoxycarbonyl, $C_{1-4}$-alkylcarbonylamino, di-$C_{1-4}$-alkylcarbonylamino, $C_{1-4}$-alkoxycarbonylamino, $C_{1-4}$-alkoxycarbonyl-($C_{1-4}$ alkyl)amino, carbamyl, $C_{1-4}$ alkylcarbamyl, and di-$C_{1-4}$-alkylcarbamyl;

each D$^3$ is independently selected from H, halogen, cyano, nitro, hydroxyl, $C_{1-6}$ alkyl, $C_{1-6}$ haloalkyl, $C_{2-6}$ alkenyl, $C_{2-6}$ alkynyl, $C_{3-14}$ cycloalkyl, $C_{3-14}$ cycloalkyl-$C_{1-4}$-alkyl, $C_{2-14}$ heterocycloalkyl, $C_{2-14}$ heterocycloalkyl-$C_{1-4}$-alkyl, $C_{6-14}$ aryl, $C_{6-14}$ aryl-$C_{1-4}$-alkyl, $C_{1-13}$ heteroaryl, $C_{1-13}$ heteroaryl-$C_{1-4}$-alkyl; wherein said $C_{1-6}$ alkyl, $C_{1-6}$ haloalkyl, $C_{2-6}$ alkenyl, and $C_{2-6}$ alkynyl are each optionally substituted by 1, 2, 3, or 4 independently selected R$^6$ groups; and wherein said $C_{3-14}$ cycloalkyl, $C_{3-14}$ cycloalkyl-$C_{1-4}$-alkyl, $C_{2-14}$ heterocycloalkyl, $C_{2-14}$ heterocycloalkyl-$C_{1-4}$-alkyl, $C_{6-14}$ aryl, $C_{6-14}$ aryl-$C_{1-4}$-alkyl, $C_{1-13}$ heteroaryl, $C_{1-13}$ heteroaryl-$C_{1-4}$-alkyl are each optionally substituted by 1, 2, 3, or 4 independently selected R$^7$ groups;

each D$^4$ is independently selected from —O—, —S—, —NR$^a$C(═O)—, —NR$^a$C(═S)—, —NR$^b$C(═O)NR$^c$—, —NR$^b$C(═S)NR$^c$—, —S(═O)—, —S(═O)$_2$—, —S(═O)NR$^a$—, —C(═O)—, —C(═S)—, —C(═O)O—, —OC(═O)NR$^a$—, —OC(═S)NR$^a$, —NR$^b$S(═O)NR$^c$—, and —NR$^b$S(═O)$_2$NR$^O$—;

each R$^4$ and R$^6$ is independently selected from halogen, cyano, nitro, hydroxyl, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, amino, $C_{1-4}$ alkylamino, di-$C_{1-4}$-alkylamino, $C_{1-4}$ alkylcarbonyl, carboxy, $C_{1-4}$ alkoxycarbonyl, $C_{1-4}$-alkylcarbonylamino, di-$C_{1-4}$-alkylcarbonylamino, $C_{1-4}$-alkoxycarbonylamino, $C_{1-4}$-alkoxycarbonyl-($C_{1-4}$ alkyl) amino, carbamyl, $C_{1-4}$ alkylcarbamyl, and di-$C_{1-4}$-alkylcarbamyl;

each R$^5$ is independently selected from halogen, cyano, nitro, hydroxyl, $C_{1-4}$ alkyl, $C_{2-4}$ alkenyl, $C_{2-4}$ alkynyl, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, amino, $C_{1-4}$ alkylamino, di-$C_{1-4}$-alkylamino, $C_{1-4}$ alkylcarbonyl, carboxy, $C_{1-4}$ alkoxycarbonyl, $C_{1-4}$-alkylcarbonylamino, di-$C_{1-4}$-alkylcarbonylamino, $C_{1-4}$-alkoxycarbonylamino, $C_{1-4}$-alkoxycarbonyl-($C_{1-4}$ alkyl)amino, carbamyl, $C_{1-4}$ alkylcarbamyl, and di-$C_{1-4}$-alkylcarbamyl;

each R$^7$ is independently selected from halogen, cyano, nitro, $C_{1-6}$ alkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, $C_{1-7}$ heteroaryl-$C_{1-4}$-alkyl, —OR$^o$, —SR$^o$, —S(═O)R$^P$, —S(═O)$_2$R$^P$, —S(═O)NR$^s$R$^t$, —C(═O)R$^P$, —C(═O)OR$^P$, —C(═O)NR$^s$R$^t$, —OC(═O)R$^P$, —OC(═O)NR$^s$R$^t$<, —NR$^s$R$^t$, —NR$^q$C(═O)R$^r$, —NR$^q$C(═O)OR$^r$, —NR$^q$C(═O)NR$^r$, —NR$^q$S(═O)$_2$R$^r$, and —NR$^P$S(═O)$_2$NR$^s$R$^t$; wherein said $C_{1-6}$ alkyl, $C_{2-6}$ alkenyl, $C_{2-6}$ alkynyl are each optionally substituted by 1, 2, 3, or 4 independently selected R' groups; and wherein said $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, $C_{1-4}$ heteroaryl-$C_{1-4}$-alkyl are each optionally substituted by 1, 2, 3, or 4 independently selected R" groups;

each R$^a$, R$^b$, R$^c$, R$^d$, R$^e$, and R$^f$ are independently selected from H, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, and $C_{1-7}$ heteroaryl-$C_{1-4}$-alkyl; wherein said $C_{1-6}$ alkyl, $C_{1-6}$ haloalkyl, $C_{2-6}$ alkenyl, and $C_{2-6}$ alkynyl are each optionally substituted by 1, 2, 3, or 4 independently selected R$^w$ groups; and wherein said $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, and $C_{1-7}$ heteroaryl-$C_{1-4}$-alkyl are each optionally substituted by 1, 2, 3, or 4 independently selected $R^x$ groups;

each $R^o$, $R^p$, $R^q$, $R^r$, $R^s$, and $R^t$ are each independently selected from H, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, and $C_{1-7}$ heteroaryl-$C_{1-4}$-alkyl; wherein said $C_{1-6}$ alkyl, $C_{1-6}$ haloalkyl, $C_{2-6}$ alkenyl, and $C_{2-6}$ alkynyl are each optionally substituted by 1, 2, 3, or 4 independently selected $R^y$ groups; and wherein said $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, and $C_{1-7}$ heteroaryl-$C_{1-4}$-alkyl are each optionally substituted by 1, 2, 3, or 4 independently selected $R^z$ groups;

each R', $R^w$ and $R^y$ is independently selected from hydroxyl, cyano, nitro, $C_{1-4}$ alkoxy, $C_{1-4}$ haloalkoxy, amino, $C_{1-4}$ alkylamino, and di-$C_{1-4}$-alkylamino; and each R", $R^x$ and $R^z$ is independently selected from hydroxyl, halogen, cyano, nitro, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

provided that the valency of each atom in the optionally substituted moieties is not exceeded.

DOTA is commercially available and has been proven safe in humans when chelated to gadolinium and used in millimolar concentrations as an MRI contrast agent (Bourrinet et al. *Invest. Radiol.* 42:63-77, 2007).

DOTA and DOTA variants chelate a wide range of metals including paramagnetic metals and radionuclides. The metal within the chelate can be any one of a wide range of metals depending upon the way in which the engineered protein will be used. Exemplary metals include yttrium, indium, gallium, gadolinium, europium, terbium, lutetium, copper, bismuth, actinium and all lanthanide metals. When the metal is a radionuclide it can be a β emitter, e.g., $^{86}Y$, $^{90}Y$, $^{186}Re$, $^{188}Re$, $^{131}I$, $^{177}Lu$, or $^{67}Cu$, an α emitter, e.g., $^{213}Bi$, $^{211}At$, $^{225}Ac$, or a low-energy electron emitter, i.e., an Auger-emitter, e.g., $^{125}I$, $^{111}In$ or $^{67}Ga$. In general, useful radionuclides include, for example, but are not limited to, $^{90}Y$, $^{111}In$, $^{67}Ga$, $^{68}Ga$, $^{177}Lu$, or $^{157}Gd^{64}Cu$, $^{67}Cu$, $^{89}Zr$, $^{47}Sc$, $^{153}Sm$, $^{166}Tb$, $^{166}Tb$, $^{166}Ho$, $^{212}Pb$, $^{212}Bi$, $^{213}Bi$, $^{225}Ac$ and $^{227}Ac$.

The metal chelates of the invention can be conjugated to one or more additional moieties, for example, a small molecule, a polypeptide or a carbohydrate. The linkage can be, for example via one of the carbons in the backbone of the macrocycle ring. A small molecule can be, for example a dye, such as Alexa Fluor® 647 or Alexa Fluor® 48; biotin or a biotin moiety. A polypeptide can be an oligopeptide, for example, a therapeutic peptide or polypeptide such as an antibody, e.g., a scFv that binds a cellular target. Exemplary carbohydrates include dextran, linear or branched polymers or co-polymers (e.g., polyalkylene, poly(ethylene-lysine), polymethacrylate, polyamino acids, poly- or oligosaccharides, dendrimers).

Nucleic Acids

The terms "nucleic acid" and "polynucleotide" may be used interchangeably herein, and refer to both RNA and DNA, including cDNA, genomic DNA, synthetic DNA, and DNA (or RNA) containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA) and portions thereof, transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs. In the context of the present invention, nucleic acids can encode an engineered protein, for example, an antibody, a mutant antibody or fragment thereof, or a fusion protein or fragment thereof.

An "isolated" nucleic acid can be, for example, a naturally-occurring DNA molecule or a fragment thereof, provided that at least one of the nucleic acid sequences normally found immediately flanking that DNA molecule in a naturally-occurring genome is removed or absent. Thus, an isolated nucleic acid includes, without limitation, a DNA molecule that exists as a separate molecule, independent of other sequences (e.g., a chemically synthesized nucleic acid, or a cDNA or genomic DNA fragment produced by the polymerase chain reaction (PCR) or restriction endonuclease treatment). An isolated nucleic acid also refers to a DNA molecule that is incorporated into a vector, an autonomously replicating plasmid, a virus, or into the genomic DNA of a prokaryote or eukaryote. In addition, an isolated nucleic acid can include an engineered nucleic acid such as a DNA molecule that is part of a hybrid or fusion nucleic acid. A nucleic acid existing among many (e.g., dozens, or hundreds to millions) of other nucleic acids within, for example, cDNA libraries or genomic libraries, or gel slices containing a genomic DNA restriction digest, is not an isolated nucleic acid.

Isolated nucleic acid molecules can be produced by standard techniques. For example, polymerase chain reaction (PCR) techniques can be used to obtain an isolated nucleic acid containing a nucleotide sequence described herein, including nucleotide sequences encoding a polypeptide described herein (i.e. an engineered protein). PCR can be used to amplify specific sequences from DNA as well as RNA, including sequences from total genomic DNA or total cellular RNA. Various PCR methods are described in, for example, *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid (as one may wish to do, for example, when making an engineered protein, for example, an antibody, a mutant antibody or fragment thereof, or a fusion protein or fragment thereof. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >50-100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring portion of an engineered protein-encoding DNA.

Two nucleic acids or the polypeptides they encode may be described as having a certain degree of identity to one another. For example, an engineered protein, for example, an antibody, a mutant antibody or fragment thereof, or a fusion protein or fragment thereof and a biologically active variant thereof may be described as exhibiting a certain degree of identity. Alignments may be assembled by locating short an engineered protein, for example, antibody sequences in the Protein Information Research (PIR) site. (http://pir-dot-georgetown-dot-edu) followed by analysis with the "short nearly identical sequences" Basic Local Alignment Search Tool (BLAST) algorithm on the NCBI website (http://www-dot-ncbi-dot-nlm-dot-nih-dot-gov/blast).

As used herein, the term "percent sequence identity" refers to the degree of identity between any given query sequence and a subject sequence. For example, a protein (e.g., an antibody), whether naturally occurring or not, can be the query sequence and a second protein, such as a mutant protein (e.g., a naturally produced antibody into which one or more mutations have been introduced) can be the subject sequence. For example, a known sequence, such as SEQ ID NO:1 can serve as the query sequence and a new protein, such as one described herein, can be the subject sequence.

To determine sequence identity, a query nucleic acid or amino acid sequence can be aligned to one or more subject nucleic acid or amino acid sequences, respectively, using the computer program ClustalW (version 1.83, default parameters), which allows alignments of nucleic acid or protein sequences to be carried out across their entire length (global alignment). See Chenna et al, *Nucleic Acids Res.* 31:3497-3500, 2003.

ClustalW calculates the best match between a query and one or more subject sequences and aligns them so that identities, similarities and differences can be determined. Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine a percent identity between a query sequence and a subject sequence, ClustalW divides the number of identities in the best alignment by the number of residues compared (gap positions are excluded), and multiplies the result by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

The nucleic acids and polypeptides described herein may be referred to as "exogenous". The term "exogenous" indicates that the nucleic acid or polypeptide is part of, or encoded by, a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

Recombinant constructs are also provided herein and can be used to transform cells in order to express an engineered protein, for example, an antibody, a mutant antibody or fragment thereof, or a fusion protein or fragment thereof. A recombinant nucleic acid construct comprises a nucleic acid encoding an engineered protein, for example, an antibody, a mutant antibody or fragment thereof, or a fusion protein or fragment thereof as described herein, operably linked to a regulatory region suitable for expressing the engineered protein, for example, an antibody, a mutant antibody or fragment thereof, or a fusion protein or fragment thereof in the cell. Thus, a nucleic acid can comprise a coding sequence that encodes any of the antibodies as set forth in SEQ ID NOs: 1-17 (e.g., in FIG. 3). In some cases, a recombinant nucleic acid construct can include a nucleic acid comprising a coding sequence, a gene, or a fragment of a coding sequence or gene in an antisense orientation so that the antisense strand of RNA is transcribed. It will be appreciated that a number of nucleic acids can encode a polypeptide having a particular amino acid sequence. The degeneracy of the genetic code is well known in the art. For many amino acids, there is more than one nucleotide triplet that serves as the codon for the amino acid. For example, codons in the coding sequence for a given fragment of an antibody, a mutant antibody or fragment thereof, or a fusion protein or fragment thereof can be modified such that optimal expression in a particular organism is obtained, using appropriate codon bias tables for that organism.

Vectors containing nucleic acids such as those described herein also are provided. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a host cell. For example, a marker can confer biocide resistance, such as resistance to an antibiotic (e.g., kanamycin, G418, bleomycin, or hygromycin). As noted above, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

The vector can also include a regulatory region. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

As used herein, the term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

Also provided herein are host cells. A host cell can be for example, a prokaryote e.g., a bacterium such as *E. coli*, or a eukaryote, e.g., yeast, insect or mammalian cell.

Methods of use: The engineered proteins disclosed herein are generally and variously useful for generating immune responses, as prophylactic vaccines or immune response-stimulating therapeutics, and in purification schemes. A patient is effectively treated whenever a clinically beneficial result ensues. This may mean, for example, a complete resolution of the symptoms of a disease, a decrease in the severity of the symptoms of the disease, or a slowing of the disease's progression.

The methods disclosed herein can be applied to a wide range of species, e.g., humans, non-human primates (e.g., monkeys), horses or other livestock, dogs, cats or other mammals kept as pets, rats, mice, or other laboratory animals. The engineered proteins described herein are useful in therapeutic compositions and regimens or for the manufacture of a medicament or for the manufacture of a medicament for use in treatment of diseases or conditions as described herein (e.g., a cancer disclosed herein or an infectious disease).

Administration and formulation: The engineered proteins described herein can be administered directly to a mammal, which we may also refer to as a "subject" or "patient." Generally, the engineered proteins can be suspended in a pharmaceutically acceptable carrier (e.g., physiological saline or a buffered saline solution) to facilitate their delivery (e.g., by intravenous administration). Encapsulation of the polypeptides in a suitable delivery vehicle (e.g., polymeric microparticles or implantable devices) may increase the efficiency of delivery. A composition can be made by combining any of the peptides provided herein with a pharmaceutically acceptable carrier. Such carriers can include, without limitation, sterile aqueous or non-aqueous solutions, suspensions, and emulsions. Examples of non-aqueous solvents include mineral oil, propylene glycol, polyethylene glycol, vegetable oils, and injectable organic esters. Aqueous carriers include, without limitation, water, alcohol, saline, and buffered solutions. Preservatives, flavorings, and other additives such as, for example, antimicrobials, anti-oxidants (e.g., propyl gallate), chelating agents, inert gases, and the like may also be present. It will be appreciated that any material described herein that is to be administered to a mammal can contain one or more pharmaceutically acceptable carriers.

Any composition described herein can be administered to any part of the host's body for subsequent delivery to a target cell. A composition can be delivered to, without limitation, the brain, the cerebrospinal fluid, joints, nasal mucosa, blood, lungs, intestines, muscle tissues, skin, or the peritoneal cavity of a mammal. In terms of routes of delivery, a composition can be administered by intravenous, intracranial, intraperitoneal, intramuscular, subcutaneous, intramuscular, intrarectal, intravaginal, intrathecal, intratracheal, intradermal, or transdermal injection, by oral or nasal administration, or by gradual perfusion over time. In a further example, an aerosol preparation of a composition can be given to a host by inhalation.

The dosage required will depend on the route of administration, the nature of the formulation, the nature of the patient's illness, the patient's size, weight, surface area, age, and sex, other drugs being administered, and the judgment of the attending clinicians. Suitable dosages are in the range of 0.01-1,000 μg/kg. Wide variations in the needed dosage are to be expected in view of the variety of cellular targets and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the engineered proteins in a suitable delivery vehicle (e.g., polymeric microparticles or implantable devices) may increase the efficiency of delivery.

The duration of treatment with any composition provided herein can be any length of time from as short as one day to as long as the life span of the host (e.g., many years). For example, an engineered protein can be administered once a week (for, for example, 4 weeks to many months or years); once a month (for, for example, three to twelve months or for many years); or once a year for a period of 5 years, ten years, or longer. It is also noted that the frequency of treatment can be variable. For example, the present engineered proteins can be administered once (or twice, three times, etc.) daily, weekly, monthly, or yearly.

An effective amount of any composition provided herein can be administered to an individual in need of treatment. The term "effective" as used herein refers to any amount that induces a desired response while not inducing significant toxicity in the patient. Such an amount can be determined by assessing a patient's response after administration of a known amount of a particular composition. In addition, the level of toxicity, if any, can be determined by assessing a patient's clinical symptoms before and after administering a known amount of a particular composition. It is noted that the effective amount of a particular composition administered to a patient can be adjusted according to a desired outcome as well as the patient's response and level of toxicity. Significant toxicity can vary for each particular patient and depends on multiple factors including, without limitation, the patient's disease state, age, and tolerance to side effects.

Any method known to those in the art can be used to determine if a particular response is induced. Clinical methods that can assess the degree of a particular disease state can be used to determine if a response is induced. The particular methods used to evaluate a response will depend upon the nature of the patient's disorder, the patient's age, and sex, other drugs being administered, and the judgment of the attending clinician.

Alternatively, a polynucleotide containing a nucleic acid sequence encoding an engineered protein can be delivered to an appropriate cell of the animal. This can be achieved by, for example, the use of a polymeric, biodegradable microparticle or microcapsule delivery vehicle, sized to optimize phagocytosis by phagocytic cells such as macrophages. For example, PLGA (poly-lactide-co-glycolide) microparticles approximately 1-10 μm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 μm and preferably larger than 20 μm).

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells. Delivery of "naked DNA" (i.e., without a delivery vehicle) to an intramuscular, intradermal, or subcutaneous site, is another means to achieve in vivo expression.

In the relevant polynucleotides (e.g., expression vectors) the nucleic acid sequence encoding the engineered protein with an initiator methionine and optionally a targeting sequence is operatively linked to a promoter or enhancer-promoter combination. Promoters and enhancers are described above, and many are well known in the art.

Polynucleotides can be administered in a pharmaceutically acceptable carrier. Pharmaceutically acceptable carriers are biologically compatible vehicles which are suitable for administration to a human or other mammalian subject (e.g., physiological saline). A therapeutically effective amount is an amount of the polynucleotide which is capable of producing a medically desirable result (e.g., a decrease in clinical motor symptoms) in a treated mammal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed. Routes of administration can be any of those listed above.

Combination Therapy: The engineered proteins of the invention can also be administered with another therapeutic agent, such as a cytotoxic agent, or cancer chemotherapeutic. Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks.

In some embodiments the methods provided contemplate the administration of combinations, or "cocktails," of different engineered proteins. Such cocktails may have certain advantages inasmuch as they contain polypeptides that exploit different effector functions. Such proteins in combination may exhibit synergistic therapeutic effects. Useful engineered proteins include those that target the EGF receptor (e.g., Cetuximab (Erbitux™)), those that target VEGF (e.g., Bevacizumab (Avastin™)) and those that target Her-2 (e.g., trastuzimab (Herceptin™)).

A cytotoxic agent refers to a substance that inhibits or prevents the function of cells and/or causes destruction of cells. The term is intended to include radioactive isotopes (e.g., $^{131}I$, $^{125}I$, $^{90}Y$ and $^{186}Re$), chemotherapeutic agents, and toxins such as enzymatically active toxins of bacterial, fungal, plant or animal origin or synthetic toxins, or fragments thereof. A non-cytotoxic agent refers to a substance that does not inhibit or prevent the function of cells and/or does not cause destruction of cells. A non-cytotoxic agent may include an agent that can be activated to be cytotoxic. A non-cytotoxic agent may include a bead, liposome, matrix or particle (see, e.g., U.S. Patent Publications 2003/0028071 and 2003/0032995 which are hereby incorporated by reference herein). Such agents may be conjugated, coupled, linked or associated with an antibody disclosed herein.

In some embodiments, conventional cancer medicaments are administered with the compositions disclosed herein. Suitable agents include those agents that promote DNA-damage, e.g., double stranded breaks in cellular DNA, in cancer cells. Any form of DNA-damaging agent know to those of skill in the art can be used. DNA damage can typically be produced by radiation therapy and/or chemotherapy. Examples of radiation therapy include, without limitation, external radiation therapy and internal radiation therapy (also called brachytherapy). Energy sources for external radiation therapy include x-rays, gamma rays and particle beams; energy sources used in internal radiation include radioactive iodine ($iodine^{125}$ or $iodine^{131}$), and from $strontium^{89}$, or radioisotopes of phosphorous, palladium, cesium, iridium, phosphate, or cobalt. Methods of administering radiation therapy are well know to those of skill in the art.

As noted, the present engineered proteins can also be used in sorting and purification schemes, and we expect such methods to be advantageous over currently available methods, such as those carried out using HPLC, as sorting and purification using the present engineered proteins should take less time. This can be important where one is purifying or isolating metal chelates that include isotopes having short half lives. Accordingly, the engineered proteins of the invention can be bound to a solid support, such as a bead, resin, or other material suitable for use with a purification column, and these substrate-bound compositions are within the scope of the present invention. To separate successfully radiolabled moieties (e.g., a chemotherapeutic agent bound to a metal chelate comprising DOTA, or an active variant thereof, and a radioactive metal ion) from unlabeled moieties, one would provide a column or similar device to which a DOTA-binding protein of the invention has been bound. A mixture (e.g., a reaction mixture) containing radiolabeled and non-radiolabeled moieties is then passed over the column (or other device) to which the DOTA-binding protein is bound. The column can be rinsed as necessary and the radiolabeled moieties can be eluted by methods known in the art (e.g., washing with solutions at low pH).

EXAMPLES

Example 1

Modeling Analysis

The PRIT models developed here are extensions of two model systems developed and described by Thurber and colleagues (*J. Nucl. Med.* 48:995-999, (2007)). The micrometastasis model uses spherical geometry and assumes diffusion-only transport. The vascularized tumor model uses cylindrical geometry around capillaries. Numerical simulations were performed in MATLAB (The Math Works, Framingham, Mass.).

PRIT simulations were performed for a 1 gram vascularized tumor and a 400 micron diameter micrometastasis assuming a 70 kg human with 3.5 liters of blood volume. The antibody is given as a bolus dose of 7 μmol at time zero. The hapten is given as a bolus dose of 350 nmol with 5 GBq initial activity at 24 h. The model implements a clearing step 2 h before hapten dosing, in which 99.9% of remaining bsAb (bispecific antibody) is cleared from the blood. Unbound hapten concentration in the blood is calculated as the initial hapten concentration minus hapten that binds to residual antibody in the blood. The model assumes a 90Y radionuclide that is 100% residualizing over the 13 day simulation period.

As noted, we mathematically modeled the effect of DOTA-binding affinity on the delivery of ionizing radiation in PRIT. Two mathematical models were implemented that simulate PRIT based on previously validated models, one that simulates antibody distribution in vascularized tumors and the other in micrometastases (Thurber et al., *J. Nucl. Med.* 48:995-999, 2007). These two types of tumors were considered separately due to different modes of transport. For micrometastases, antibody and hapten diffuses into the tumor mass from the surrounding interstitial fluid. While there may be some transport from surrounding interstitial fluid into the edges of large vascularized tumors, the majority of antibody and hapten transport occurs across the tumor vasculature.

We extended both models to account for hapten kinetics, assuming a bsAb with one hapten binding site and one antigen binding site with specificity to carcinoembryonic antigen (CEA), with a 15 h internalization half-time (Schmidt et al., *Cancer Immunol. Immunother. Apr.* 12, 2008). We used an initial bsAb blood concentration of 2 micromolar as an input variable. We expect this initial concentration to essentially saturate the antigen binding sites for vascularized tumors from both our modeling results and from Fenwick and colleagues (Fenwick et al., *Int. J. Cancer* 44:1017-1027, 1989) demonstrating that antibody doses of several hundreds of micrograms or more are required to obtain saturation in a mouse xenograft model. The model implementation assumes bsAb dosing at time 0, followed by a clearing/blocking step at 22 h and hapten dosing at 24 h, with an initial hapten blood concentration of 100 nanomolar. Our model predicts that this hapten dose will saturate the pretargeted bsAb binding sites in the vascularized tumor. Note that bsAb and hapten doses are orders of magnitude above those predicted to saturate micrometastases. The model assumes a 70 kg man and 2-compartment pharmacokinetic parameters for antibody and hapten.

PRIT model simulations were run, varying the hapten dissociation rate while keeping the association rate constant. We looked at hapten concentration in the tumor as a function of time and total cumulative activity assuming a 90Y radionuclide with a 64 h half-life. Hapten retention in vascular tumors (FIG. 1A) and micrometastases (FIG. 1B) were predicted over a hapten $K_D$ range of six orders of magnitude. The model assumes that DOTA chelates are 100% residualized after internalization; internalization of hapten-antibody-CEA complexes results in the plateau observed in FIG. 1 at long times. We relaxed this assumption and ran simulations with a non-residualizing rate constant and found that the total cumulative activity was consistently lower for all affinities, but the same trend for varying affinities was retained. We also looked at the effect of varying the association rate while maintaining a constant $K_D$ and found no significant difference in hapten retention for typical hapten association rates ($5\times10^5$-$5\times10^7$ $M^{-1}s^{-1}$), demonstrating that the relevant parameter is $K_D$.

For the aforementioned PRIT conditions, we predict that a hapten $K_D$ greater than 100 pM will allow significant hapten retention for both vascularized tumors and micrometastases.

Example 2

DOTA Complexes

DOTA (Macocyclics M-140) and DOTA-Bn (S-2-(4-Aminobenzyl)-1,4,7,10-tetraazacyclododecane tetraacetic acid; Macrocyclics B-200) were dissolved in 0.4 M sodium acetate, pH 5.2, to prepare stock solutions.

DOTA-Bn-biotin was synthesized by dissolving Amine-PEG3-Biotin (Pierce 21347) and p-SCN-Bn-DOTA (S-2-(4-Isothiocyanatobenzyl)-1,4,7,10-tetraazacyclododecane-tetraacetic acid; Macocyclics B-205) in dimethyl sulfoxide (DMSO) with a 10-fold molar excess of triethylamine (VWR #EM-TX 1200-5). The reaction mixture was vortexed at room temperature for 3 hours, and then purified by high performance liquid chromatography (HPLC). HPLC purification was performed on a C-18 reverse-phase column (Agilent Model 1100 HPLC, 1×25 cm, buffer A=0.05% trifluoroacetic acid (TFA), buffer B=0.0425% TFA in 80% acetonitrile, 2-100% B gradient for 98 minutes). Flow through was monitored by absorbance detection at 280 nanometers. Fractions containing DOTA-Bn-biotin were confirmed using matrix assisted laser desorption instrument time of flight (MALDI-TOF) mass spectrometry (Applied Biosystems Model Voyager DE-STR). Chemical purity was assessed by analytical HPLC (Agilent Model 1100 HPLC, 2.1×150 mm, buffer A=0.05% TFA, buffer B=0.0425% TFA in 80% acetonitrile, 2-100% B gradient for 45 minutes). DOTA-Bn-biotin concentration was determined using a biotin quantitation kit (Pierce 28005) following the manufacturer's instructions.

DOTA-alkyl-biotin was synthesized following the procedure of Takenouchi et al. (*J. Organic Chem.* 58:1955-1958, 1993) starting with the compound H-Lys(Boc)-OMe (Bachem, E-1620). H-Lys(Boc)-OMe was treated stepwise with methyl bromoacetate and diethylenetriamine to obtain tert-butyl 4-(3,12-dioxo-1,4,7,10-tetraazacyclododecan-2-yl)butylcarbamate. Borane-THF complex was used to reduce the carboxylic amides followed by trifluoroacetic acid Boc deprotection to obtain 4-(1,4,7,10-tetraazacyclododecan-2-yl)butan-1-amine. This compound was subsequently reacted with biotin-xx, SSE (Invitrogen, B-6352) in DMSO with a 10 fold molar excess of triethylamine for 3 hours vortexing at room temperature. In all synthesis steps compounds were purified by HPLC and confirmed by mass spectrometry with a Waters (Milford, Mass.) LCT electrospray time-of-flight (ES-TOF) liquid chromatography mass spectrometry (LC/MS) or by MALDI-TOF as described above.

Metal complexes of each DOTA derivative (see FIG. 2 for chemical structures) were prepared as follows. Yttrium nitrate hexahydrate, lutetium (III) chloride hexahydrate, indium (III) chloride, gallium (III) nitrate hydrate, and gadolinium (III) chloride hexahydrate were purchased from Sigma and prepared as stock solutions in 0.4 M sodium acetate pH 5.2. To a 2 mM (for DOTA and DOTA-Bn) or 400 μM (for DOTA-Bn-biotin) solution of the chelating agent, a 5-fold molar excess of the metal stock solution was added and chelated by overnight rotation at room temperature. The pH was adjusted to 7 with 10 M NaOH and the complex was diluted with phosphate buffered saline with 0.1% bovine serum albumin (PBSA) to a final concentration of 1 mM (for DOTA and DOTA-Bn) or 200 μM (for DOTA-Bn-biotin). For gadolinium chelates, an identical metal loading procedure was used except that the complexation reaction took place at 80° C. for 12 h in a thermocycler. Complete complexation of the chelator was confirmed by LC/MS using a 75 μm×150 mm C18 column (Magic C18 from Michrom Bioresources).

Example 3

Kinetic Characterization $K_D$ Measurements for DOTA-Bn-biotin-metal: Equilibrium dissociation constants ($K_D$) for binding of yeast surface-displayed scFv to biotinylated DOTA complexes at 37° C. were determined in triplicate by titration as described by Chao et al. (*Nat. Protoc.* 1:755-768, 2006). Briefly, yeast expressing an scFv clone on their surface were grown, washed with PBSA and incubated with various concentrations of DOTA-Bn-biotin-metal long enough to allow for at least a 95% approach to equilibrium. Generally, $5\times10^5$ induced cells were used for each concentration point. When antigen concentrations less than 10 pM were assayed, the titration was performed with $2.5\times10^4$ induced and $7.5\times10^5$ non-induced cells to ensure antigen excess over the scFv without requiring impractically large volumes. The addition of non-induced cells aids pelleting during centrifugation (Hackel et al., *J. Mol. Biol.* 381:1238-1252, 2008). When antigen concentrations greater than 100 nM were used, non-specific antigen binding to the yeast surface was taken into account. Yeast expressing an irrelevant scFv on their surface were treated in the same manner as the yeast displaying the scFv of interest, and mean total phycoeryhthrein fluorescence (MFUtot) due to non-specific binding was measured by flow cytometry and averaged over three replicates. This value was subtracted from the MFUtot for the yeast of interest, and the data was fit by least-squares regression.

$K_D$ Measurements for DOTA-metal and DOTA-Bn-metal. To determine the $K_D$ for scFv binding to nonbiotinylated haptens, the above protocol was modified to a competition-based assay as follows. After determining the $K_D$ for scFv binding to DOTA-Bn-biotin-Y, a titration was set up with 100 pM DOTA-Bn-biotin-Y, $2.5\times10^5$ cells per tube, and varying concentrations of the nonbiotinylated complex. Incubation, staining, and flow cytometry analysis was the same as that for biotinylated antigen. MFUtot as a function of the concentration of the nonbiotinylated antigen ([Ag]), a normalization constant (MFUrange), the minimal total mean fluorescence (MFUmin), the $K_D$ for DOTA-Bn-biotin-Y (KD, biot), DOTA-Bn-biotin-Y concentration ([Agbiot]), and the $K_D$ for the antigen of interest ($K_D$) follows this modified equation:

$$MFU_{tot} = MFU_{min} + \frac{MFU_{range} \times [Ag_{biot}]}{K_{D,biot} + [Ag_{biot}] + \left(\frac{K_{D,biot}}{K_D}\right)[Ag]}$$

The data was fit by least squares regression as before, varying MFUmin, MFUrange and $K_D$.

Dissociation Kinetics. To determine the dissociation rate, $k_{off}$, for DOTA-Bn-biotin complexes, cells were induced and washed as above, and 1×107 cells were incubated in 1 mL PBSA with 1 nM DOTA-Bn-biotin-metal for 1 h to reach saturation. Subsequently, the yeast were washed with 1 mL PBSA, resuspended in 1 mL PBSA with 1 μM (excess) non-biotinylated antigen as competitor and split into 100 μL aliquots. These aliquots were incubated at 37° C. for different lengths of time, then washed with cold PBSA and left on ice. All samples were simultaneously stained with streptavidin-phycoerythrein for 10-20 min and analyzed by flow cytometry. The data was fit to the following equation by least squares regression, varying $MFU_{min}$, $MFU_{range}$ and $k_{off}$:

$$MFU_{tot}=MFU_{min}+MFU_{range}e^{-k_{off}t}$$

For nonbiotinylated antigens, the procedure was identical except that initial saturation was with the nonbiotinylated antigen and DOTA-Bn-biotin-metal was used as competitor. The data followed the expression $$MFU_{tot}=MFU_{min}+MFU_{range}(1-e^{-k_{off}t})$$

Example 4

Affinity Maturation

The 2D12.5 scFv served as our starting point and was subjected to nine rounds of directed evolution by random mutagenesis and subsequent selection for improved binding using yeast surface display as described by Chao and colleagues (*Nat. Protoc.* 1:755-768, 2006) and adapted as follows.

Preparation of DOTA Complexes. DOTA Chelates were Incubated with Yttrium, gadolinium, lutetium, gallium, and indium overnight at for metal complexation. The products were analyzed by LC-MS to verify that the entire DOTA chelate had been loaded with metal. All samples exhibited peak(s) corresponding to the expected mass of the metal complex with characteristic isotope patterns. The samples did not contain detectable uncomplexed DOTA.

Mutagenesis. To counteract the mutational bias of error-prone PCR, mutagenesis at each round was also performed with the Mutazyme™ mutagenesis kit (Stratagene) according to the manufacturer's instructions, and the resulting mutagenized DNA was pooled with that obtained by error-prone PCR. All other steps were carried out according to standard methods (see Chao et al.).

Selection. Each round of mutagenesis resulted in a library size of $0.5\text{–}4\times10^7$ and was sorted 2-3 times by flow cytometry for improved binders. At least five times, the estimated library diversity was labeled for cell sorting. Staining was performed by equilibrium incubation at a biotinylated DOTA-Y concentration of approximately ⅓ of the average $K_D$ of the previous library (in early rounds) or by saturation with antigen followed by dissociation for 2-3 dissociation halftimes (in later rounds), and subsequent labeling with streptavidin-phycoerythrein. To label for full-length scFv expression, the yeast were also stained with a mouse anti-HA (clone 12CA5, Roche Applied Science) or a mouse anti-cmyc (clone 9e10, Covance) primary antibody and a goat anti-mouse Alexa Fluor® 647 (Invitrogen) secondary antibody. Yeast expressing the best 0.01-0.1% of binders were collected. Periodically, the antigen was alternated between DOTA-Bn-biotin-Y and DOTA-alkyl-biotin-Y.

Figure 3A:
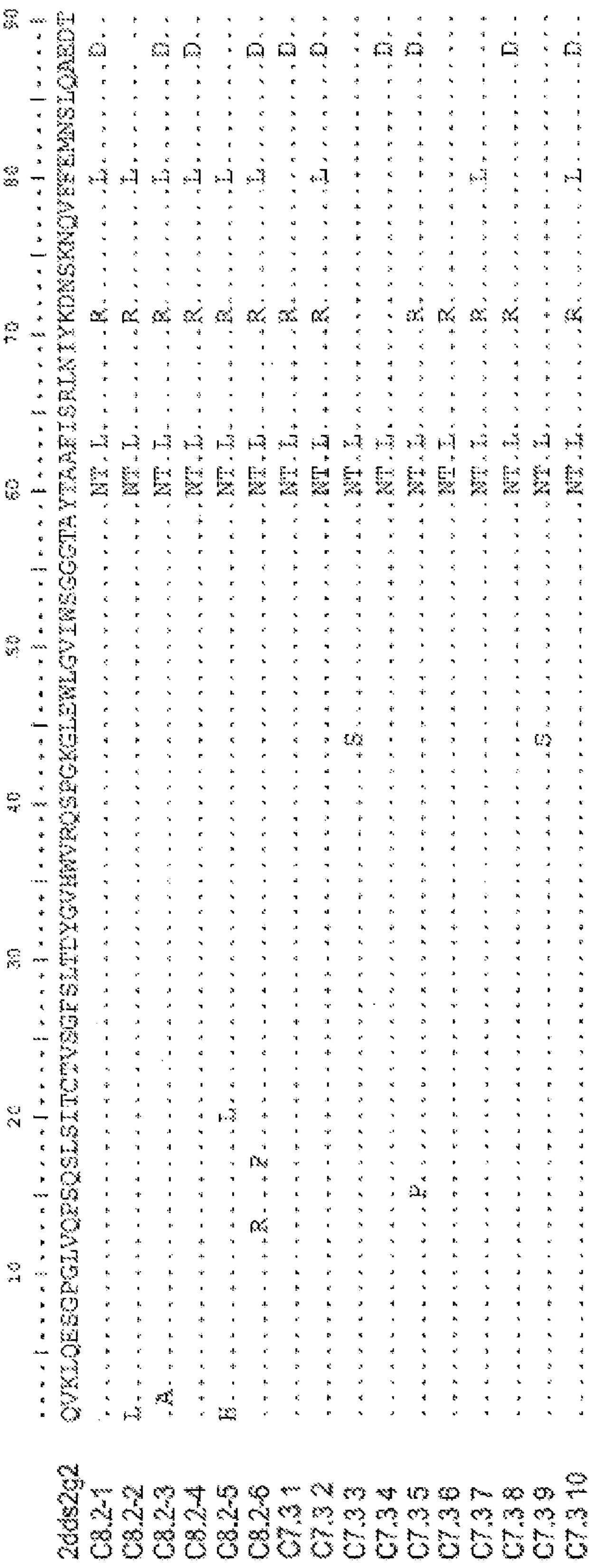
FIG. 3 is a representation of the sequences of mutants obtained from an affinity maturation screen of 2D12.5 scFV (SEQ ID NO:1). 2ddsg2 is the 2D12.5 scFV amino acid sequence with amino acid substitutions at positions 88 (N88E), 111 (Q111C), and 179 (L179C) (SEQ ID NO:2). Dots represent the same residue as the 2ddsg2 sequence. Various mutant sequences are: mutant C8.2-1 (is represented by SEQ ID NO:3; residues 1-244 of SEQ ID NO:3 are represented by SEQ ID NO:4); C8.2 2 (represented by SEQ ID NO:5; residues 1-244 of SEQ ID NO:5 are represented by SEQ ID NO:6); C8.2 3 (represented by SEQ ID NO:7; residues 1-244 of SEQ ID NO:7 are represented by SEQ ID NO:8); C8.2 4 (represented by SEQ ID NO:9; residues 1-244 of SEQ ID NO:9 are represented by SEQ ID NO:10); C8.2 5 (represented by SEQ ID NO:11; residues 1-244 of SEQ ID NO:11 are represented by SEQ ID NO:12); C8.2 6 (represented by SEQ ID NO:13; residues 1-244 of SEQ ID NO:13 are represented by SEQ ID NO:14); C7.3 1 (represented by SEQ ID NO:15; residues 1-244 of SEQ ID NO:15 are represented by SEQ ID NO:16); C7.3 2 (represented by SEQ ID NO:17; residues 1-244 of SEQ ID NO:17 are represented by SEQ ID NO:18); C7.3 3 (represented by SEQ ID NO:19; residues 1-244 of SEQ ID NO:19 are represented by SEQ ID NO:20); C7.3 4 (represented by SEQ ID NO:21; residues 1-244 of SEQ ID NO:21 are represented by SEQ ID NO:22); C7.3 5 (represented by SEQ ID NO:23; residues 1-244 of SEQ ID NO:23 are represented by SEQ ID NO:24); C7.3 6 (represented by SEQ ID NO:25; residues 1-244 of SEQ ID NO:25 are represented by SEQ ID NO:26); C7.3 7 (represented by SEQ ID NO:27; residues 1-244 of SEQ ID NO:27 are represented by SEQ ID NO:28); C7.3 8 (represented by SEQ ID NO:29; residues 1-244 of SEQ ID NO:29 are represented by SEQ ID NO:30); C7.3 9 (represented by SEQ ID NO:31; residues 1-244 of SEQ ID NO:31 are represented by SEQ ID NO:32); C7.3 10 (represented by SEQ ID NO:33; residues 1-244 of SEQ ID NO:33 are represented by SEQ ID NO:34).
Figure 3B:
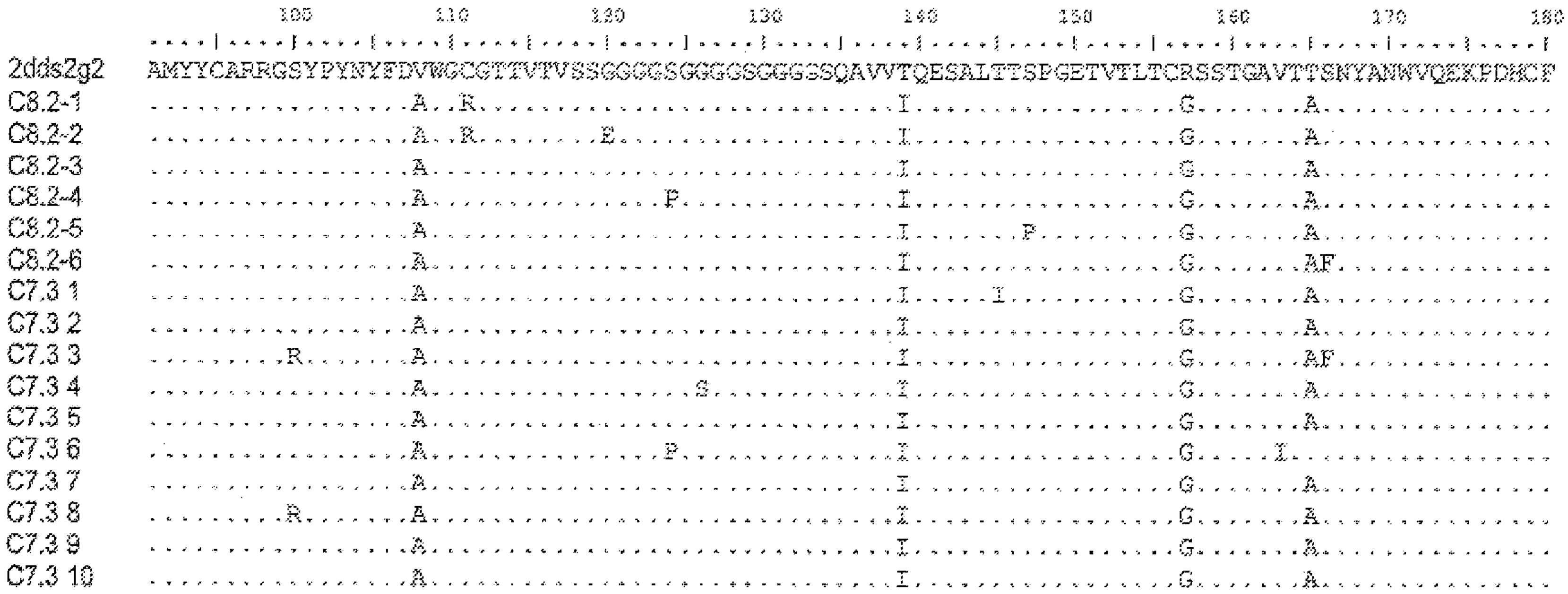
Figure 3C:
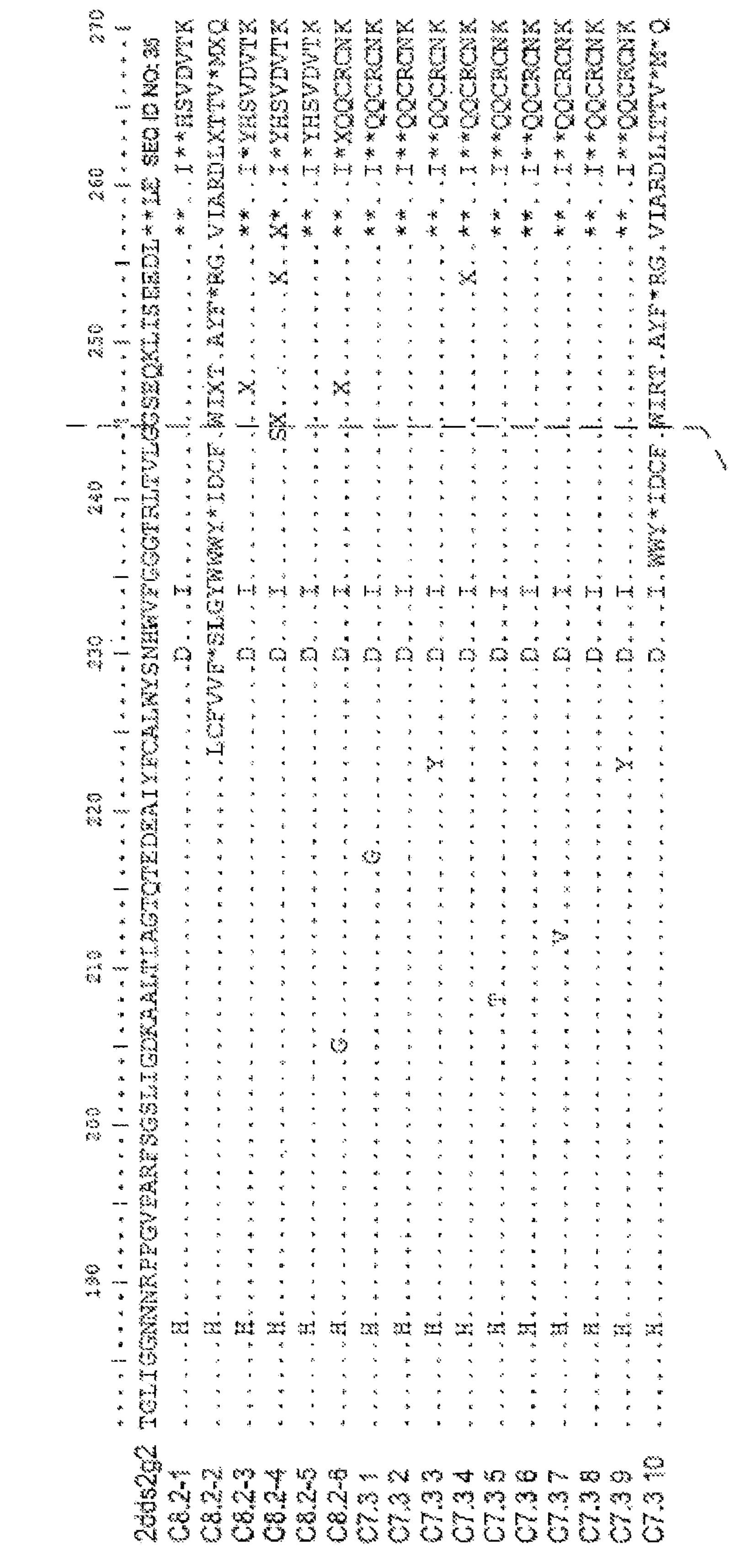
Figure 4:
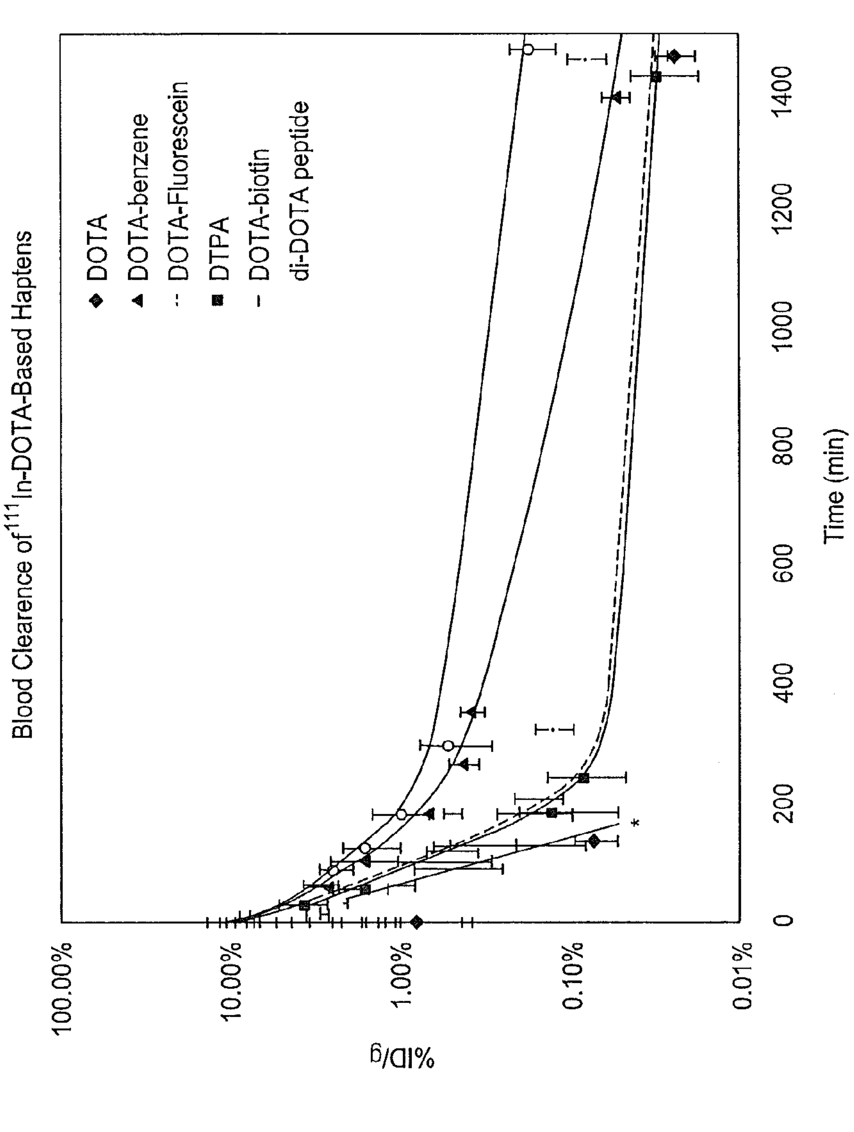
FIG. 4 is a graph depicting the results of an analysis of blood clearance of $^{111}$In-DOTA-based haptens.
Figure 5:
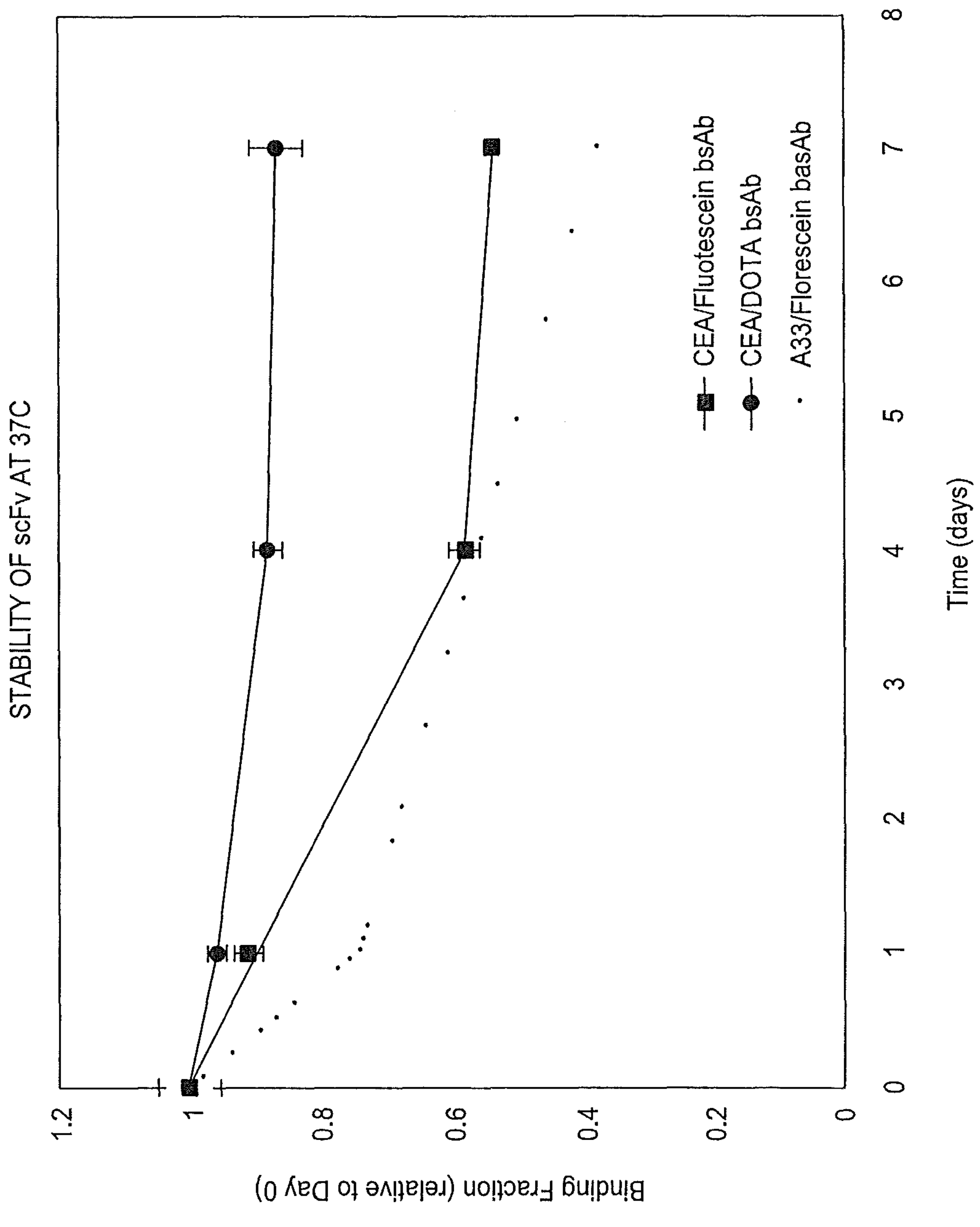
FIG. 5 is a graph depicting the results of an analysis of the stability of bispecific antibodies at 37° C.
Figure 6:
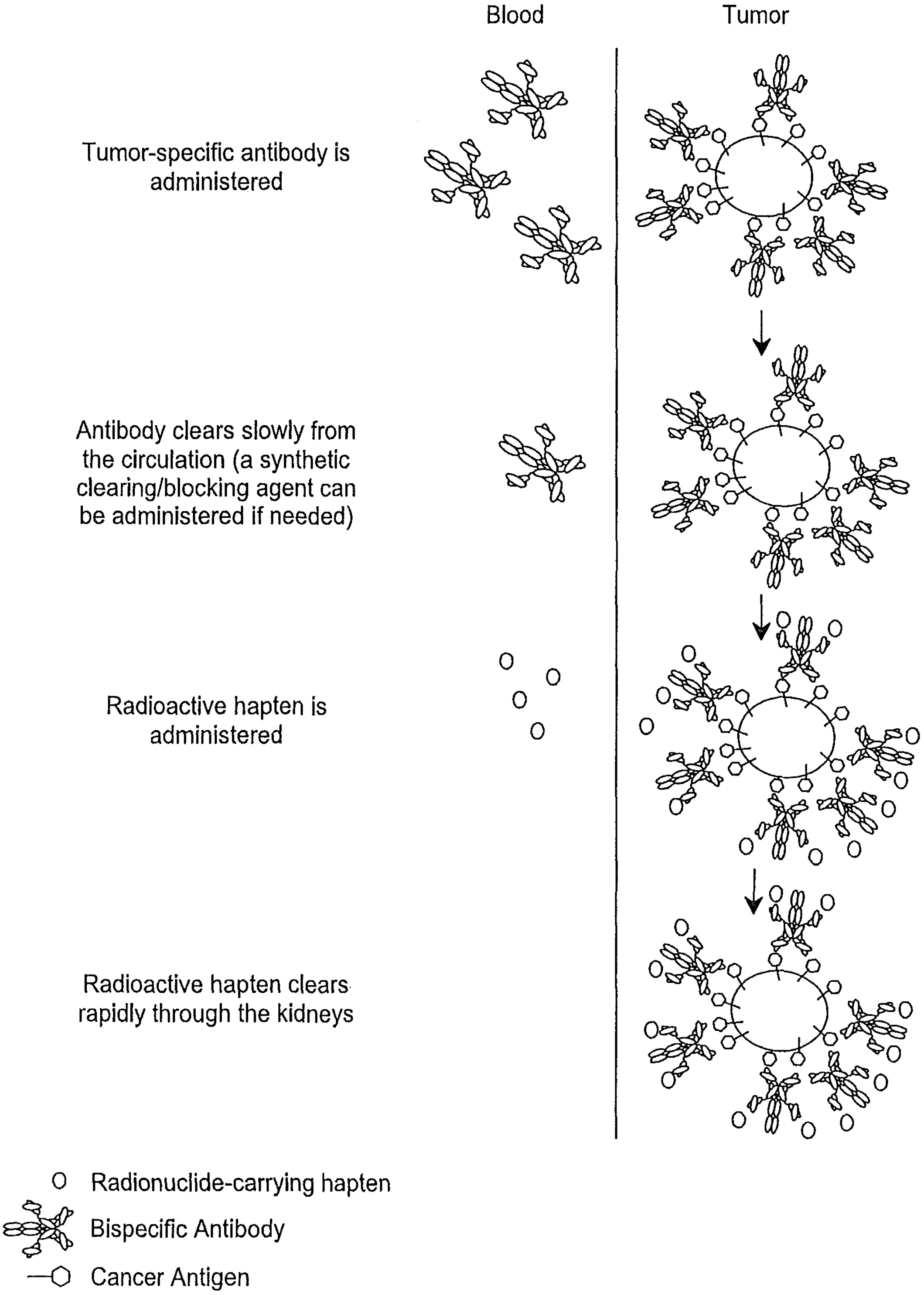
FIG. 6 is a schematic illustrating the process of pretargeted radioimmunotherapy.
Figure 7:
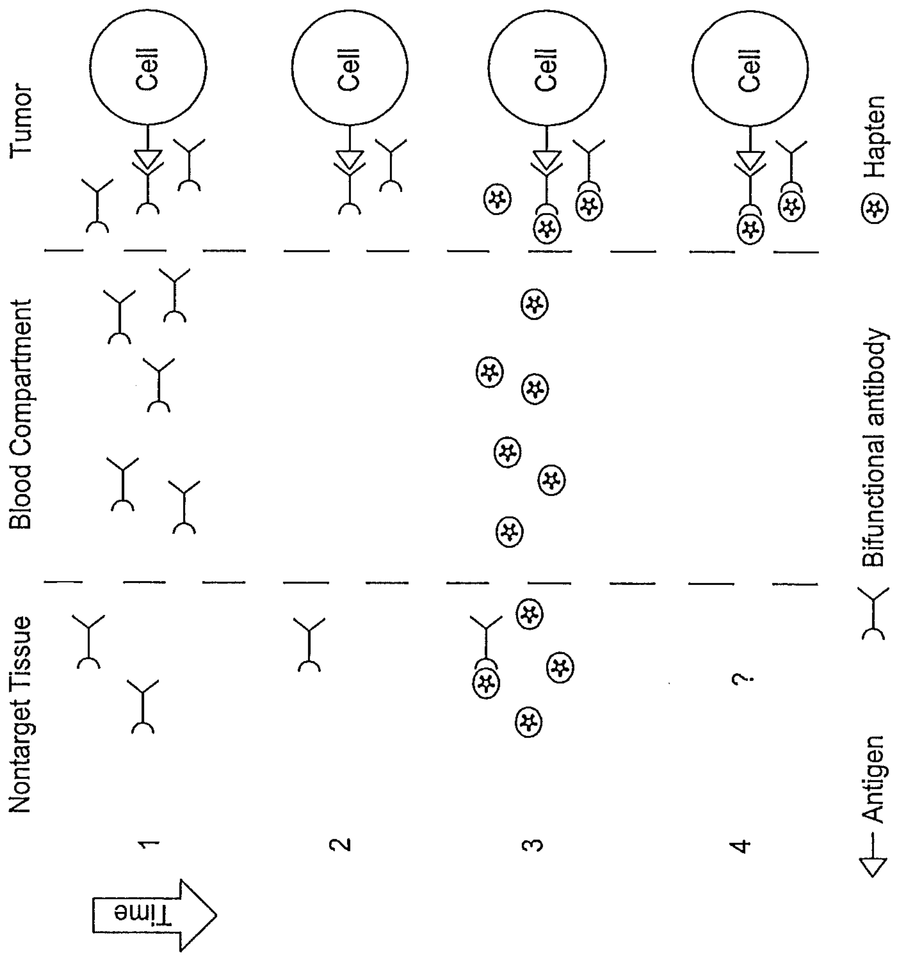
FIG. 7 is also a schematic illustrating PRIT with a bifunctional antibody.

Disulfide stabilization and glycosylation knockout. The N-linked glycosylation site in the heavy chain of the scFv was removed and a disulfide bond between the heavy and light chain was introduced during the seventh mutagenesis of the affinity maturation. This was accomplished by introducing through PCR site-directed mutagenesis the mutations N88E or N88D, Q111C, and L179C (numbering corresponds to the scFv sequence; FIG. 3C).

Selection of clones. Individual clones were isolated by transforming XL-1 blue chemically competent *E. coli* (Stratagene) with plasmid DNA isolated from the yeast library (Zymoprep™ II Kit, Zymo research) and plating on agar plates containing ampicillin. Individual colonies were picked and grown in liquid medium overnight and plasmid DNA was isolated using the Qiagen Miniprep kit. The plasmid DNA was sequenced and transformed back into yeast with the EZ Yeast™ transformation kit (Zymo Research). Clonal yeast cultures were grown and their kinetic parameters determined.

Example 5

Analysis of Affinity-Matured Antibodies

We affinity matured the 2D12.5 antibody fragment against biotinylated DOTA-Y by directed evolution. The gene encoding the 2D12.5 DOTA IgG in an scFv format (FIG. 3C) was synthesized from its published sequence (Corneillie et al., *J. Am. Chem. Soc.* 125:15039-15048, 2003). In total, nine rounds of affinity maturation were performed. Yeast expressing 2D12.5 variants were labeled with either DOTA-Bn-biotin-Y or DOTA-alkyl-biotin-Y (FIG. 2) followed by streptavidin-phycoerythrein and sorted by flow cytometry to select the highest affinity clones. The antigen was periodically switched to minimize selection of variants with mutations that conferred binding improvement to the linker region. During the seventh mutagenesis, we introduced an intramolecular disulfide bond between the heavy and light variable regions of the scFv (Reiter et al., *Nat. Biotechnol* 14:1239-1245, 1996) and removed the N-linked glycosylation site in the heavy chain. These additional mutations may improve stability and result in simpler downstream processing of the scFv.

Amino acid sequences for a panel of mutants are shown in FIG. 3. Sequences and kinetic constants were determined for several clones from libraries 8.2 (8 rounds of mutagenesis followed by 2 sorts) and 9.3 (9 rounds of mutagenesis and 3 sorts). All clones from library 9.3 had lost the disulfide bond between the heavy and light chain and were consequently discarded. Of the clones from library 8.2, C8.2.5 retained the disulfide bond and bound most tightly to DOTA-Bn-biotin-Y.

The sequence of the high-affinity C8.2.5 scFv differed from 2D12.5ds (the original 2D12.5 scFv with the addition of the intramolecular disulfide bond and removed glycosylation site) at 15 amino acid positions. The spatial distribution in the crystal structure of wild-type 2D12.5 is depicted in FIGS. 3A and 3B. Only one mutation, N53(L)H (numbering corresponds to the 2D 12.5 antigen-binding fragment (Fab) for which the crystal structure was determined), occurred within 5 Angstroms of the bound hapten, indicating that most mutations enhanced affinity via subtle structural perturbations remote from the binding interface.

The kinetic properties of both 2D12.5ds and C8.2.5 were characterized and are summarized in Tables 1 and 2. The affinity of the scFv to DOTA-Bn-biotin-Y increased by three orders of magnitude, from nanomolar to single-digit picomolar. The dissociation half-time for DOTA-Bn-biotin-Y increased from 5.5 min for 2D12.5ds to just over 5 hours for C8.2.5 (Table 2).

The high-affinity clone C8.2.5 bound DOTA-Bn-biotin-Y, DOTA-Bn-Y, and DOTA-Y with equilibrium dissociation constants of 8.2±1.9 pM, 15.4±2.0 pM, and 103±35 pM, respectively, indicating that there were some binding interactions between the scFv and the benzene ring and biotin linker region. The affinity differences between these various yttrium chelates were reflected in their dissociation half-lives (Table 2).

Remarkably, DOTA complexes of lutetium and gadolinium were bound by C8.2.5 similarly to those of yttrium (see Table 1). The high-affinity scFv also bound indium and gallium chelates with nanomolar affinity. All DOTA-metal chelates were bound by C8.2.5 with about an order of magnitude weaker affinity than the respective DOTA-Bn metal chelate, providing additional evidence of binding interactions between the scFv and the benzene ring.

TABLE 1

Equilibrium dissociation constants for yeast surface-displayed scFvs bound to DOTA complexes

| scFv | Hapten | Metal | $K_D$* | n |
|---|---|---|---|---|
| 2D12.5ds | DOTA-Bn-Biotin | Y | 3.7 ± 3.6 nM | 3 |
| C8.2.5 | DOTA-Bn-Biotin | Y | 8.2 ± 1.9 pM | 3 |
| | DOTA-Bn | Y | 15.4 ± 2.0 pM | 3 |
| | | Lu | 10.8 ± 2.5 pM | 3 |
| | | Gd | 34.0 ± 5.3 pM | 2 |
| | | In | 1.01 ± 0.04 nM | 2 |
| | | Ga | 52 ± 12 nM | 2 |
| | DOTA | Y | 103 ± 35 pM | 3 |
| | | Lu | 390 ± 14 pM | 2 |
| | | Gd | 149 ± 6 pM | 2 |
| | | In | 23.7 ± 3.7 nM | 2 |
| | | Ga | 216 ± 26 nM | 2 |

*$K_D$ given as mean ± SD.

TABLE 2

Dissociation half-lives for yeast surface-displayed scFvs bound to DOTA complexes

| scFv | Hapten | Metal | Dissociation half-life* |
|---|---|---|---|
| 2D12.5ds | DOTA-Bn-Biotin | Y | 5.5 ± 1.3 |
| C8.2.5 | DOTA-Bn-Biotin | Y | 302 ± 13 |
| | DOTA-Bn | Y | 53.1 ± 2.3 |
| | DOTA | Y | 3.5 ± 0.7 |
| | | Lu | 3.8 ± 0.4 |

*Calculated as IN(2)/$K_{off}$ and given in minutes as mean ± SD for n = 3 experiments.

Example 6

Construction of Bispecific Antibodies

The bispecific format was designed as an scFv fusion to the C-terminus of the light chain of an IgG. The heavy chain is the same as that of an IgG1 and was subcloned into the mammalian expression vector gWiz™, purchased from Aldevron (Fargo, N. Dak.). The light chain is constructed as leader-FLAG-VL-$C_K$-$(Gly_4Ser)_2$-scFv-cmyc, where VL is the variable light domain, $C_K$ is the kappa light chain constant domain, and FLAG and cmyc are N- and C-terminal epitope tags, respectively. It was cloned into a separate gWiz™ plasmid. Both plasmids were transiently co-expressed in HEK293 cells (cat. no. R790-07) purchased from Invitrogen (Carlsbad, Calif.). HEK293 cells were grown in flasks on an orbital shaker platform at 140 rpm at 37° C., 5% CO2 and subcultured following the manufacturer's protocol. Co-transfection was performed with polyethyleneimine (PEI) as the transfection reagent. Briefly, HEK293 cells were subcultured to a cell density of 0.5–0.7×$10^6$ cells/mL 24 h before transfection. Immediately before transfection, cell density was adjusted to 1×$10^6$ cells/mL. 500 μg of each purified plasmid (1 mg/mL) was added to 19 mL OptiPRO™ (Invitrogen). 2 mL of 1 mg/mL PEI pH 7.0 (MW 25,000) purchased from Polysciences (Warrington, Pa.) dissolved in water was added to 18 mL OptiPRO™. Both solutions were incubated at room temperature for 5 min. The DNA/OptiPRO™ solution was added to the PEI/OptiPRO™ solution and incubated for 10 min at room temperature and added drop-wise to 1 L HEK293 culture. The supernatant was collected 6-8 d after transfection. Antibodies were purified by protein A chromatography (Thermo Fisher Scientific, Rockford, Ill.) following the manufacturer's instructions.

Specific constructs were made by overlap extension PCR and QuikChange™ mutagenesis. The Sm3e/C825 bsAb was cloned and produced as described above using the VH and VL domains from the affinity-matured anti-CEA Sm3e scFv (Graff et al., *Protein Eng. Des. Sel.* 17:293-304, 2004) and the disulfide-stabilized C8.2.5 scFv. The Sm3e/4 m5.3 bsAb substituted a 4 m5.3 scFv that is a femtomolar fluorescein binder (Boder et al., *Proc. Natl. Acad. Sci. USA* 97:10701-10705, 2000) disulfide stabilized by introducing two cysteine residues, S43C in the VL domain and Q105C in the VH domain (Reiter et al., *Nat. Biotechnol.* 14:239-1245, 1996). The A33/4 m5.3 bsAb uses the VH and VL domains from an A33 humanized Fab fragment (Rader et al. *JBC* 275:13668-13676, 2000) for the IgG binding domains. Sm3e IgG and A33 IgG plasmids were produced by introducing two stop codons in the light chain immediately following the CK sequence via QuikChange™ PCR. The C-terminus of the A33 IgG light chain was extended by an 18 amino acid peptide (($G_4S)_2$LPETGGSG), to make the construct A33 IgG+ peptide. A33 IgG+ peptide was disulfide stabilized by introducing two different pairs of cysteine residues, VL G100C and VH G44C (dsl) and VL V43C and VH Q105C (ds2) (Reiter et al. 1996).

Example 7

Plasmid Design and Expression in HEK293 Cells

Figure 8:
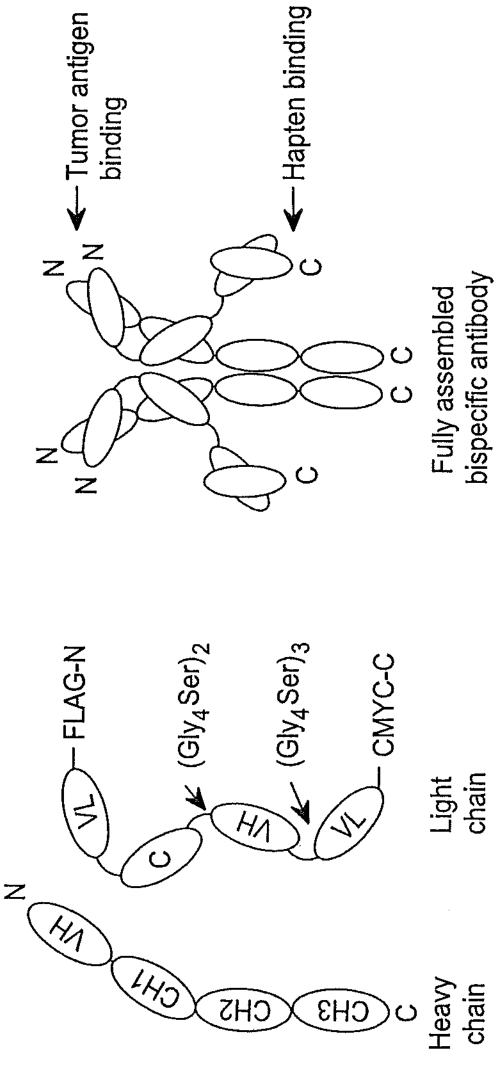
FIG. 8 is a schematic illustrating the design of an IgG light chain C-terminal scFv fusion protein. The light chain is modified with an scFv fusion to the C-terminus, while a completely naïve heavy chain is preserved.

We have designed a bispecific antibody as a C-terminal fusion to the light chain of an IgG (FIG. 8). The heavy chain is identical to that of an IgG. The light chain is constructed by extending an IgG light chain with a C-terminal $(Gly_4Ser)_2$ linker followed by an scFv. In this study, the light chain is constructed with an N-terminal FLAG tag and C-terminal cmyc tag for characterization purposes. The fully assembled bsAb contains two heavy and two light chains, and is tetravalent with two IgG binding domains and two scFv binding domains.

We synthesized a bsAb of this format that binds to the carcinoembryonic antigen (CEA) and to complexes of the metal chelate, DOTA. The Sm3e/C825 bsAb was constructed from an Sm3e IgG and a DOTA-binding scFv, C8.2.5, by cloning heavy and light variable domains from the picomolar affinity Sm3e scFv (Graff et al., *Protein Eng. Des. Sel.* 17:293-304, 2004) into a plasmid containing human IgG1 constant heavy domains and kappa constant light chain domain. The C8.2.5 scFv was subsequently cloned into the light chain plasmid immediately following the C-terminus of the Cκ gene. The heavy and light chain expression plasmids were transiently co-transfected into HEK293 mammalian cells. Secreted antibody was purified from cell culture supernatants by protein A chromatography. Yields of both Sm3e IgG and Sm3e/C825 bsAb were ~5-7 mg/L.

Non-reducing SDS-page gel electrophoresis of purified bsAb displays a species with a molecular weight of ~200 kDa. Under reducing conditions, the bsAb gives rise to two bands, both at around 50 kDa, as the scFv fusion increases the molecular weight of the light chain to ~50 kDa. Size exclusion chromatography of purified bsAb shows a single dominant peak with a small amount of higher molecular weight species, similar to that observed for recombinant IgG and for IgG purified from human plasma.

Example 8

In Vivo Tumor Targeting

Here, we present a novel three-step method for PRIT using an IgG-scFv bispecific antibody, a dextran-based clearing agent, and radiolabeled DOTA, and test proof-of-principle of this system in a xenograft mouse model. In addition, we use this system to analyze in vivo the affect of small molecule affinity on tumor uptake. Biodistribution and tumor uptake were evaluated in xenograft mice with CEA-positive and CEA-negative tumors for $^{177}$Lu-DOTA, $^{111}$In-DOTA-Bn, and $^{111}$In-DOTA after pretargeting with an anti-CEA bsAb. Kidney, liver, and bone marrow doses were estimated using standard Medical Internal Radiation Dose (MIRD) methodology. The PRIT method resulted in tumor uptake of $^{177}$Lu-DOTA of ~14% ID/g at 24 h and 48 h, tumor-to-kidney ratios of ~20 at 24 h and 48 h, and tumor-to-blood ratios of greater than 300 at 24 h and 48 h. An affinity of ~100 pM resulted in 8-fold higher tumor uptake at 24 hours than an affinity of ~1 nM, and 28-fold higher uptake than ~10 nM affinity.

Reagents. 1,4,7,10-Tetraazacyclododecane-1,4,7,10-tetraacetic acid (DOTA), S-2-(R-Aminobenzyl)-1,4,7,10-tetraazacyclododecane tetraacetic acid (DOTA-Bn) and S-2-(4-Isothiocyanatobenzyl)-1,4,7,10-tetraazacyclododecane tetraacetic acid (DOTA-SCN) were purchased from Macrocyclics (Dallas, Tex.). All other chemicals were purchased from Sigma-Aldrich (St. Louis, Mo.) or Thermo Fisher Scientific (Waltham, Mass.) unless specified otherwise.

Synthesis of dextran-based blocking agent. 5 mg (10 nmol) of 500 kDa amino dextran purchased from Invitrogen (Carlsbad, Calif.) with 136 moles of amine per mole dextran was reacted with 3.7 mg (5.3 μmol) DOTA-SCN in 1 mL DMSO with 1.9 μL (13.6 μmol) TEA overnight at room temperature with mild vortexing. The dextran reaction mixture was diluted with 14 mL 0.4 M sodium acetate pH 5.2 and 53 μmol yttrium nitrate was added. The mixture was incubated overnight at 37° C., dialyzed against water, and then dried down by vacuum centrifugation. The dried dextran compound was resuspended in PBS and purified by size exclusion chromatography using a Superdex™ 75 10/300 GL column. Fractions containing the dextran compound were combined, dialyzed against water twice, dried by vacuum centrifugation, resuspended in saline and 0.2 μm filtered. The final dextran-DOTA-Y contained approximately 130 DOTA molecules as assessed by a TNBSA assay (Thermo Fisher Scientific, Rockford, Ill.).

Radiolabeling. DOTA compounds were dissolved at 0.5 mM in ammonium acetate pH 5.6. 1-2 mCi $^{177}LuCl_3$ (PerkinElmer, Waltham, Mass.) or $^{111}InCl_3$ (Cardinal Health, Dublin, Ohio) were added to the metal chelate and incubated for 1-2 h at 85-95 C. The radiolabeled compounds were purified by RP-HPLC (Humblet et al., *Contrast Media Mol. Imaging.* 1:196-211, 2006; Misra et al., *J. Nucl. Med.* 48:1379-1389, 2007) with gamma detection on a 4.6×75 mm Symmetry C18 column using a linear gradient from 0% to 40% B over 15 minutes, at a flow rate of 1 mL/min, where A=10 mM TEAA and B=methanol. The purified compounds were dried under vacuum, resuspended in saline, and filter-sterilized.

IgG and bsAb proteins were conjugated to p-SCN-Bn-DTPA (Macrocyclics) as described (Cooper et al., *Nat. Protoc.* 1:314-317, 2006). Concentrated DTPA-labeled protein was incubated with ~1 mCi $^{111}InCl_3$ for 30 minutes at room temperature. The protein was diluted with 500 μL saline and concentrated to approximately 50 μL using Vivaspin 5000 MWCO spin columns (Sartorius Stedim Biotech, Aubagne, France). The $^{111}$In-labeled protein was diluted with 500 μL saline and concentrated twice more.

$^{111}$In-DOTA-dextran was prepared by synthesizing dextran-DOTA as described above, without loading with cold yttrium. Dextran-DOTA was incubated with 1-2 mCi $^{111}InCl_3$ for 1 h at 37° C. followed by concentration and dilution with saline as described above.

Animal models. All animal handling was performed in accordance with BIDMC IACUC guidelines. Male NCRU-nu/nu mice were purchased from Taconic Farms (Germantown, N.Y.). For biodistribution and tumor uptake, 100-150 μCi $^{177}$Lu- or $^{111}$In-labeled hapten was injected intravenously into the mice. Blood was collected from the tail vein using micro-capillary tubes and counted on a model 1470 Wallac Wizard™ (Perkin Elmer, Wellesley, Mass.) 10-detector gamma counter. Mice were euthanized by intraperitoneal injection of pentobarbital followed by cervical dislocation, a method consistent with the recommendations of the Panel on Euthanasia of the American Veterinary Medical Association. Organs and tumors were resected, washed in PCS three times, weighed, and counted as described above.

Dosimetry. Radiation doses absorbed by normal tissues other than the red marrow were calculated according to the MIRD scheme. Percent injected activity in tumor, kidneys, liver, blood, and whole-body were calculated from activity measurements. The activity at time 0 was assumed to be 4% ID/g in the kidney and liver, 50% ID/g in the blood, 0% ID/g in the tumor and 100% in the whole-body. Isotope decay-adjusted activity was integrated over time, with a conservative assumption that the 48 h organ % ID remained constant thereafter. S values for $^{90}$Y and $^{177}$Lu were used to calculate dosimetry estimates in an adult male reference (Stabin and Siegel, *Health Phys.* 85:294-310, 2003). The red marrow dose was calculated as described (Wessels et al., *J. Nucl. Med.* 45:1725-1733, 2004) from blood activity measurements. The activity in the whole-body was used to estimate the total body cumulative activity used for cross-dose calculations. Tumor doses were calculated from self-dose only using S-factors for a unit density sphere of size 500 g (the average LS174T tumor size scaled by 2000).

Imaging. SPECT/CT (single photon emission computed tomography/computed tomography) scans and image analyses were performed using a rodent scanner (NanoSPECT/CT™, Bioscan, Washington, D.C.) equipped with an 8 W x-ray source running at 45 kV (177 μA), and a 48 μm pitch CMOS-CCD x-ray detector. Mice were anesthetized in an anesthetic chamber with isoflurane and transferred to a bed on a gantry for imaging where gas anesthesia was maintained for the duration of the scan. After acquisition of a CT topogram, helical micro SPECT was performed using a four-headed gamma camera outfitted with multi-pinhole collimators (1.4 mm) and a total scan time of 45 minutes. SPECT images were acquired over 360 degrees in 24 projections each using a 256×256 frame size (1.0 mm pixels). Images were reconstructed with Bioscan HiSPECT™ iterative reconstruction software and fused with CT images. Immediately after scanning, mice were sacrificed and tissues and tumors weighted and counted as described above.

Results. The Sm3e/C825 bsAb was produced and purified as described above. 24 h biodistribution of the bsAb and the parent Sm3e IgG in male nude mice bearing CEA-positive (LS174T) and CEA-negative (C6) tumors demonstrated similar specific accumulation in the antigen-positive tumor with ~4-fold higher uptake than the antigen-negative tumor. In addition, high activity remained in the blood at 24 h, as expected, due to slow blood clearance of Fc-containing compounds.

Mice pretargeted with 500 μg bsAb were injected with $^{111}$In-DOTA-Bn 24 h later. 4 h biodistribution showed significantly higher activity in all organs due to binding to bsAb. Of particular note is the high activity in the blood and low tumor to blood ratio. The high blood activity motivated the development of a clearing/blocking agent.

We engineered a dextran-based blocking agent, using a 500 kDa aminodextran (~136 amino groups per dextran molecule) conjugated to DOTA. The resulting compound contained approximately 130 DOTA molecules per dextran. The dextran-DOTA compound was loaded with non-radioactive yttrium and, when injected into pretargeted mice one hour prior to hapten administration, resulted in hapten blood clearance essentially identical to that of hapten alone. This suggests essentially complete blocking/clearance of residual bsAb in the blood. Dextran-DOTA was radiolabeled with $^{111}$In to characterize the in vivo properties of the dextran agent alone. Biodistribution and blood clearance of $^{111}$In-DOTA-dextran was analyzed in tumor-bearing mice. The dextran agent clears very rapidly from the blood and exhibits very high uptake in the liver and spleen at 4 h post-injection (p.i.).

We next tested a protocol involving all three reagents to determine the efficacy of our engineered PRIT system. We intravenously injected tumor-bearing mice with 500 μg bsAb followed by 250 μg of dextran-DOTA-Y clearing agent 24 h later. After an additional 1 h, 100-150 μCi $^{177}$Lu-DOTA was injected intravenously. At 4 h post-injection of radiolabeled DOTA, tumor uptake was 7.44+/−0.41% ID/g in the antigen-positive tumor, 84-fold higher than the tumor uptake observed for $^{177}$Lu-DOTA alone. Activity was also higher in non-tumor tissue due to binding of $^{177}$Lu-DOTA to residual bsAb in the extravascular compartment. Tumor uptake in the antigen-negative tumor was 9.82+/−0.35% ID/g at 4 h, similar to the antigen-positive tumor due to nonspecific uptake from enhanced permeability and retention (EPR) of the bsAb. Over time, the tumor activity in the antigen-negative tumor decreased to 4.23+/−0.54% ID/g at 24 h and 2.89+/−2.28% ID/g at 48 h while the tumor activity in the antigen-positive tumor increased to 14.3+/−1.8% ID/g at 24 h and remained essentially constant at 48 h. The LS174T tumor to blood ratio increased from 18+/−2 at 4 h to 380+/−90 at 24 h and was greater than 450 at 48 h. At 48 h, the blood activity was not measurable above background. The LS174T tumor to kidney ratio increased from approximately 8 at 4 h to about 20 at 24 and 48 h. SPECT/CT images confirmed the quantitative biodistribution data with high PSECT signal in the CEA-positive tumors, lower signal in the CEA-negative tumor and no observable signal in non-tumor tissue.

From the PRIT organ biodistribution data, the radiation dose to the kidney, liver, red marrow, and antigen-positive tumor was estimated for a 70 kg man for $^{90}$Y and $^{177}$Lu. It should be noted that these estimates are generated from mouse biodistribution data and are thus approximations; human clinical data will be required for more accurate dosimetry. The estimated doses to the kidney, liver, and red marrow were calculated from both the self-dose and cross-dose, wherein the whole-body activity was used to determine the cross-dose. The estimated dose to the tumor was determined from self-dose only. The dose limiting toxicities (TD5/5) for the liver, kidney, and red marrow estimated from external beam radiation were 30 Gy, 23 Gy, and 1.5 Gy, respectively (Emami et al., *Int. J. Radiat. Oncol. Biol. Phys.* 21:109-122, 1991). From the radiation dose estimates, the dose-limiting organ is predicted to be the red marrow for both $^{90}$Y-DOTA and $^{177}$Lu-DOTA haptens. At a red marrow dose of 1.5 Gy, the estimated dose to the tumor is 98 Gy for $^{90}$Y and 156 Gy for $^{177}$Lu. A dose of greater than 50 Gy is generally thought to be sufficient to eradicate most tumors (Govindan et al., *Pharm. Sci. Technolo. Today* 3:90-98, 2000).

The pretargeted protocol described above was used to analyze the effect of affinity on the tumor uptake of radiolabeled DOTA. The bsAb exhibits affinities of ~10 nM for $^{111}$In-DOTA, ~1 nM for $^{111}$In-DOTA-Bn, ~100 pM for $^{177}$Lu-DOTA, and ~10 pM for $^{177}$Lu-DOTA-Bn. The 24 h organ/tissue biodistribution was determined in tumor-bearing mice with each of the four radiolabeled DOTA compounds. SPECT/CT images of one mouse from each set show that at least single digit nanomolar affinity is needed to observe signal in the antigen-positive tumor. The 24 h activity in the LS174T tumor increased from 0.5+/−0.1% ID/g for ~10 nM affinity to 1.6+/−0.3% ID/g for ~1 nM affinity to 14.3+/−1.8% ID/g for ~100 pM affinity. The tumor activity for ~10 pM affinity is not significantly different than that of ~100 pM affinity. The activity in the C6 antigen-negative tumor increased with affinity, presumably due to nonspecific uptake of bsAb. The activity in the non-tumor tissues is also higher for the higher affinity compounds due to the higher affinity binding to residual bsAb. The tumor to kidney ratio increased from 1.2+/−0.4 for ~10 nM to 17+/−3 for ~100 pM but then decreased to 10+/−2 for ~10 pM affinity due to higher uptake in the kidney but similar tumor uptake.

The experimental results of 24 h tumor uptake versus affinity were compared to mathematical predictions based on a previously published compartmental model of tumor uptake (Schmidt and Wittrup, *Mol. Cancer. Ther.* 8:2861-2871, 2009). Vascular permeability was estimated from the two-pore model of the capillary wall for a 1 kDa molecule. The surface density was estimated to be $2\times10^5$ DOTA binding sites per cell based on the 24 h tumor accumulation of bsAb, the 24 h activity of the scFv in serum, and the 15 h internalization rate of CEA resulting in approximately half of the accumulated bsAb to be internalized and therefore inaccessible to binding. The blood clearance parameters were calculated from a biexponential fit of the in vivo blood clearance measured for $^{177}$Lu-DOTA.

The experimental results compared well to the model prediction with the 24 h tumor uptake increasing significantly from 1 nM to 100 pM affinity and then reaching a plateau with an additional improvement in affinity from 100 pM to 10 pM resulting in no significant improvement in affinity from 100 pM to 10 pM resulting in no significant improvement in 24 h tumor activity.

Discussion. Here we present a new method for pretargeted readioimmunotherapy that uses an IgG-scFv bsAb, a dextran-based blocking agent, and radiolabeled DOTA. The engineered PRIT system was tested in xenograft mice bearing CEA-positive and CEA-negative tumors. The bsAb exhibits ~100 pM affinity for $^{177}$Lu-DOTA. $^{177}$Lu-DOTA has previously been shown to exhibit very rapid whole-body clearance from mice. Here we demonstrate high LS174T tumor uptake and retention of $^{177}$Lu-DOTA with fast clearance from non-tumor tissue resulting in the highest reported tumor-to-blood and tumor-to-kidney ratios at 48 h p.i. for CEA targeting.

A significant amount of $^{177}$Lu-DOTA uptake is observed in the CEA-negative tumors at early times. Enhanced permeability and retention (EPR) results in nonspecific tumor accumulation of high-molecular weight compounds. While approximately 4-fold higher bsAb uptake is observed in LS174T tumors versus C6 tumors, the difference in hapten uptake at early times will be less because a significant fraction of the bsAb localized to the LS174T tumors will be inaccessible due to the 15 h internalization half-life of CEA (Schmidt et al., *Cancer Immunol. Immunother.,* 2008), while all bsAb in the C6 tumors will be accessible to hapten binding. This is consistent with the observation of similar activities in the two tumors at early times. At later times, unbound antibody intravasates out of the CEA-negative tumor while CEA-bound antibody in the LS174T tumors internalizes $^{177}$Lu-DOTA compounds where the radiolabel is trapped within the cell.

The PRIT approach presented here originates from a rational engineering design perspective. We used mathematical modeling to predict the affinity necessary for efficient hapten capture and retention at the site of the tumor. We then engineered an IgG-like bsAb to retain slow blood clearance resulting in high tumor uptake, retain potentially beneficial secondary immune function, and to allow for production and purification identical to that of an IgG. We designed our system to use simply DOTA as the hapten, with no additional synthesis or modification required and thus eliminating issues with linker cleavage and peptide stability (van Gog et al., *Nucl. Med. Biol.* 25:611-619, 1998; van Schaijk et al., *Clin. Cancer Res.* 11:7130s-7136s, 2005). DOTA chelated to gadolinium has been administered to human subjects in millimolar concentrations and has an established safety profile. DOTA metal chelates exhibit rapid blood clearance and whole-body clearance is observed in mice and humans (Le Mignon et al., *Invest. Radiol.* 25:933-937, 1990). When systematically compared to other DOTA-based compounds, $^{177}$Lu-DOTA exhibits slightly lower liver and intestine uptake at 4 h p.i. compared to radiolabeled DOTA-biotin and DOTA-Bn in normal CD1 mice. This suggests that DOTA exhibits essentially complete renal clearance while DOTA-biotin and DOTA-Bn exhibit some clearance through bile. This effect may be more or less pronounced in humans.

The non-tumor tissue clearance of DOTA is not nearly as fast in mice pretargeted with bsAb, even with the addition of the dextran clearing agent, due to incomplete clearance resulting in residual antibody. Multiple doses of the clearing agent or infusion of the clearing agent over a period of time would likely result in more complete bsAb clearance from non-tumor tissue, as residual bsAb in the extravascular space will recycle back into the bloodstream over time (Press et al., *Blood* 98:2535-2543, 2001). A lower mass of dextran may also improve bsAb clearance; however, improved clearance will need to be balanced with possible tumor uptake of smaller agents resulting in blocked hapten binding sites.

We have found excellent tumor:blood ratios, which were demonstrated despite an exceptionally high dose of bsAb. Other studies of pretargeting methods report decreasing tumor:blood ratios with increasing bsAb doses (Sharkey et al., *Nat. Med.* 11:1250-1255, 2005; van Schaijk et al., *Clin. Cancer Res.* 11:7130s-7136s, 2005). Our method results in a high number of hapten binding sites in the tumor at the time of hapten dosing. This is important, as the number of hapten binding sites is directly related to the number of radioisotopes that can be captured and retained at the site of the tumor, impacting the maximum possible dose. While three-step pretargeted radioimmunotherapy adds complexity over two-step procedures, it allows higher doses of bsAb to be administered resulting in higher achieved tumor doses as well as more homogenous distribution within the tumor. In addition, it allows for possible secondary immune effects resulting from the retained Fc domain that may prove significant (Sharkey et al., *J. Nucl. Med.* 50:444-453, 2009). Two-step approaches may be sufficient for molecular imagining leading to improved cancer screening and staging (Sharkey et al., *Nat. Med.* 11:1250-1255, 2005; Sharkey et al., *Radiology* 246: 497-507, 2008). However, it is anticipated that the increased number of hapten binding sites afforded by three-step approaches will prove important for therapy.

A number of embodiments of the invention have been described. Nevertheless, it will be understood that various modifications may be made without departing from the spirit and scope of the invention. Accordingly, other embodiments are within the scope of the following claims.

What is claimed is:

1. A bispecific antibody comprising a (a) (i) a first polypeptide chain comprising the variable light chain region of an immunoglobulin that specifically binds a target molecule fused with or without a linker to a single chain variable fragment (scFv) that specifically binds a metal chelate comprising DOTA or an active variant thereof, wherein the scFv comprises the heavy and light chain CDR sequences of a mutant scFv comprising the amino acid sequence selected from the group consisting of SEQ ID NOs: 4, 6, 8, 10, 12, 14, 16, 18, 20, 22, 24, 26, 28, 30, 32, and 34; and (ii) a second polypeptide chain comprising a variable heavy chain region of the immunoglobulin of (a)(i) that specifically binds the target molecule; or (b) (i) a first polypeptide chain comprising the variable heavy chain region of an immunoglobulin that specifically binds a target molecule fused with or without a linker to a single chain variable fragment (scFv) that specifically binds a metal chelate comprising DOTA or an active variant thereof, wherein the scFv comprises the heavy and light chain CDR sequences of a mutant scFv comprising the amino acid sequence selected from the group consisting of SEQ ID NOs: 4, 6, 8, 10, 12, 14, 16, 18, 20, 22, 24, 26, 28, 30, 32, and 34; and (ii) a second polypeptide chain comprising the variable light chain region of the immunoglobulin of (b)(i) that specifically binds the target molecule.

2. The bispecific antibody of claim 1, wherein the target molecule is a cancer antigen or an antigen expressed by a virus, bacterial cell, or parasite.

3. The bispecific antibody of claim 1, wherein the scFv specifically binds the metal chelate comprising DOTA with a Kd of about 1 pM-1 nM.

4. The bispecific antibody of claim 1, wherein the mutant scFv comprises the amino acid sequence set forth in SEQ ID NO: 4.

5. The bispecific antibody of claim 1, wherein the mutant scFv comprises the amino acid sequence set forth in SEQ ID NO: 6.

6. The bispecific antibody of claim 1, wherein the mutant scFv comprises the amino acid sequence set forth in SEQ ID NO: 8.

7. The bispecific antibody of claim 1, wherein the mutant scFv comprises the amino acid sequence set forth in SEQ ID NO: 10.

8. The bispecific antibody of claim 1, wherein the mutant scFv comprises the amino acid sequence set forth in SEQ ID NO: 12.

9. The bispecific antibody of claim 1, wherein the mutant scFv comprises the amino acid sequence set forth in SEQ ID NO: 14.

10. The bispecific antibody of claim 1, wherein the mutant scFv comprises the amino acid sequence set forth in SEQ ID NO: 16.

11. The bispecific antibody of claim 1, wherein the mutant scFv comprises the amino acid sequence set forth in SEQ ID NO: 18.

12. The bispecific antibody of claim 1, wherein the mutant scFv comprises the amino acid sequence set forth in SEQ ID NO: 20.

13. The bispecific antibody of claim 1, wherein the mutant scFv comprises the amino acid sequence set forth in SEQ ID NO: 22.

14. The bispecific antibody of claim 1, wherein the mutant scFv comprises the amino acid sequence set forth in SEQ ID NO: 24.

15. The bispecific antibody of claim 1, wherein the mutant scFv comprises the amino acid sequence set forth in SEQ ID NO: 26.

16. The bispecific antibody of claim 1, wherein the mutant scFv comprises the amino acid sequence set forth in SEQ ID NO: 28.

17. The bispecific antibody of claim 1, wherein the mutant scFv comprises the amino acid sequence set forth in SEQ ID NO: 30.

18. The bispecific antibody of claim 1, wherein the mutant scFv comprises the amino acid sequence set forth in SEQ ID NO: 32.

19. The bispecific antibody of claim 1, wherein the mutant scFv comprises the amino acid sequence set forth in SEQ ID NO: 34.

20. The bispecific antibody of claim 1, wherein the scFv is a humanized scFv.

21. The bispecific antibody of claim 1, wherein the immunoglobulin is a humanized immunoglobulin.

22. The bispecific antibody of claim 1, wherein the scFv is fused with or without a linker to the C-terminus of the variable light chain region.

23. The bispecific antibody of claim 1, wherein the first polypeptide chain of (a) further comprises a light chain constant region and the scFv is fused with or without a linker to the C-terminus of the light chain constant region.

24. The bispecific antibody of claim 23, wherein the scFv is fused to the C-terminus of the light chain constant region via a linker.

25. The bispecific antibody of claim 1, wherein the first polypeptide chain of (a) comprises a variable heavy chain region of an immunoglobulin and the second polypeptide chain of (b) comprises a variable light chain region, and wherein the scFv is fused to the C-terminus of the variable heavy chain region with or without a linker.

26. The bispecific antibody of claim 25, wherein the first polypeptide chain of (a) further comprises a heavy chain constant region and the scFv is fused with or without a linker to the C-terminus of the heavy chain constant region.

27. The bispecific antibody of claim 26, wherein the scFv is fused via a linker to the C-terminus of the heavy chain constant region.

28. The bispecific antibody of claim 26, wherein the heavy chain constant region comprises a CH1 domain.

29. The bispecific antibody of claim 26, wherein the heavy chain constant region comprises a CH2 and CH3 domain.

30. The bispecific antibody of claim 1, wherein the active DOTA variant is a structure selected from the group consisting of:

(a)

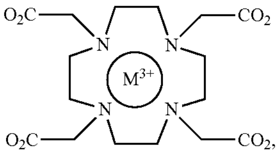

(b)

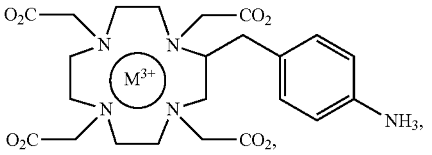

(c)

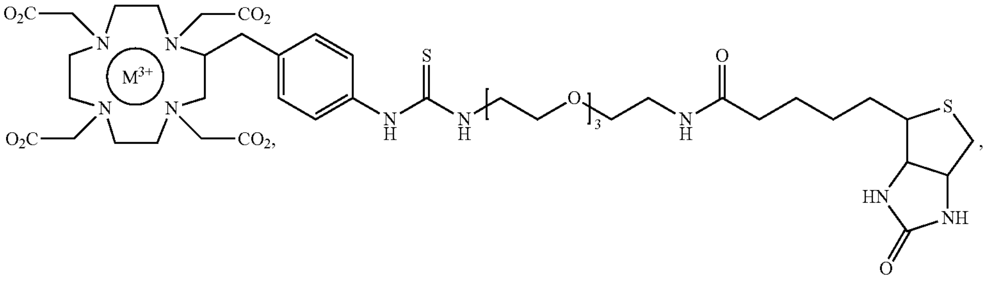

and (d)

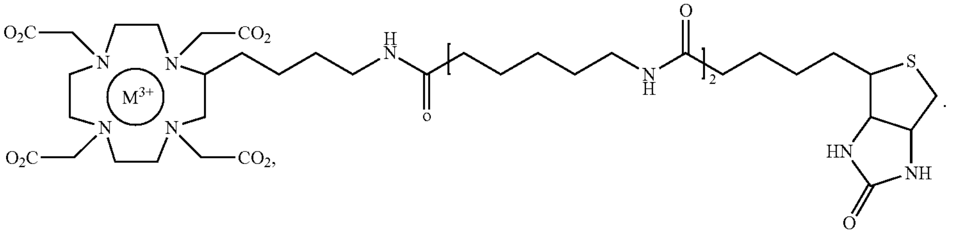

31. A bispecific antibody comprising (a) a first polypeptide chain comprising a variable light chain region of an immunoglobulin that specifically binds a target molecule fused with or without a linker to a single chain variable fragment (scFv) that specifically binds a metal chelate comprising DOTA, wherein the scFv comprises the heavy and light chain CDR sequences of a mutant scFV comprising the amino acid sequence set forth in SEQ ID NO: 12; and (b) a second polypeptide chain comprising a variable heavy chain region of the immunoglobulin of (a) that specifically binds the target molecule.

32. The bispecific antibody of claim 31, wherein the first polypeptide chain of (a) further comprises a light chain constant region and the scFv is fused with or without a linker to the C-terminus of the light chain constant region.

33. The bispecific antibody of claim 32, wherein the scFv is fused to the C-terminus of the light chain constant region via a linker.

34. The bispecific antibody of claim 32, wherein the second polypeptide chain of (b) further comprises a heavy chain constant region.

35. The bispecific antibody of claim 34, wherein the heavy chain constant region comprises a CH1 domain.

36. The bispecific antibody of claim 34, wherein the heavy chain constant region comprises a CH2 and CH3 domain.

37. The bispecific antibody of claim 31, wherein the target molecule is a cancer antigen or an antigen expressed by a virus, bacterial cell, or parasite.

38. The bispecific antibody of claim 31, wherein the immunoglobulin is a humanized immunoglobulin.

39. A composition comprising the bispecific antibody of claim 31 and a pharmaceutically acceptable carrier.

40. A composition comprising the bispecific antibody of claim 1 and a pharmaceutically acceptable carrier.

* * * * *